US007341728B2

(12) United States Patent
Tan et al.

(10) Patent No.: US 7,341,728 B2
(45) Date of Patent: Mar. 11, 2008

(54) INTERNALISATION OF VIRUS INTO CELLS

(75) Inventors: Yin Hwee Tan, Vancouver (CA); Yee Joo Tan, Singapore (SG); Siew Pheng Lim, Singapore (SG); Seng Gee Lim, Singapore (SG); Wan Jin Hong, Singapore (SG); Phuay Yee Goh, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 191 days.

(21) Appl. No.: 10/478,444

(22) PCT Filed: May 24, 2002

(86) PCT No.: PCT/CA02/00762

§ 371 (c)(1),
(2), (4) Date: Jun. 4, 2004

(87) PCT Pub. No.: WO02/094874

PCT Pub. Date: Nov. 28, 2002

(65) Prior Publication Data

US 2004/0241640 A1    Dec. 2, 2004

(30) Foreign Application Priority Data

May 24, 2001  (GB) .................................. 0112652.3

(51) Int. Cl.
*A61K 39/00* (2006.01)
*A61K 39/42* (2006.01)

(52) U.S. Cl. .............................. 424/192.1; 424/159.1; 424/160.1; 424/161.1; 424/178.1; 435/5; 435/7.1

(58) Field of Classification Search ............. 424/192.1, 424/208.1, 228.1
See application file for complete search history.

(56) References Cited

U.S. PATENT DOCUMENTS 5,308,750 A * 5/1994 Mehta et al. .................. 435/5
5,817,789 A * 10/1998 Heartlein et al. .......... 536/23.4

FOREIGN PATENT DOCUMENTS

| WO | WO 92/08983 | * | 5/1992 |
| WO | WO 93/18185 |   | 9/1993 |
| WO | WO 96/23881 |   | 8/1996 |
| WO | WO 01/93549 |   | 12/2001 |

OTHER PUBLICATIONS

Houdebine, L. Production of pharmaceutical proteins from transgenic animals, Journal of Biotechnology, 1994, 34:269-287.*
Orkin et al. Report and Recommendations of the Panel to Assess the NIH Investment in Research on Gene Therapy, available from http://www.nih.gov/news/panelrep.html, 39 pages, (1995).*
Verma et al. Gene therapy—promises, problems and prospects, Nature, 1997, 389:239-242.*
Tan et al. Virology, 2003, 315:80-92.*
Bitton et al., "Characterization of T cell-expressed chimeric receptors with antibody-type specificity for the CD4 binding site of HIV-1 gp120." Euro. J. Immunol. 28(12), 4177-4187, 1998.
Chen et al., "Quantitative detection of hepatitis B virus DNA in human sera by branched-DNA signal amplification" J. Virol. Methods 53(1) 131-137, 1995.
Choo et al., "Genetic organization and diversity of the hepatitis C virus" PNAS USA 88, 2451-2455, 1991.
Collawn et al., Transplanted LDL and mannose-6-phosphate receptor internalization signals promote high-efficiency endocytosis of the transferrin receptor. EMBO J., 10(11), 3247-3253, 1991.
Flint et al., "Characterization of Hepatitis C Virus E2 Glycoprotein Interaction with a Putative Cellular Receptor, CD81" J. Virol. 73, 6235-6244, 1999.
He and Landau, "Use of a Novel Human Immunodeficiency Virus Type 1 Reporter Virus Expressing Human Placental alkaline Phosphatase to Detect an Alternative Viral Receptor" J. Virol. 69, 4587-4592, 1995.
Higginbottom et al., "Identification of amino acid residues in CD81 critical for interaction with hepatitis C virus envelope glycoprotein E2." J. Virol., 74(8), 3642-3649, 2000.
Khakoo et al., "A clinical evaluation of a new method for HBV DNA quantitation in patients with chronic hepatitis B" J. Med. Virol. 50(2) 112-116, 1996.
Lanford et al., "Demonstration of in Vitro Infection of Chimpanzee Hepatocytes with Hepatitis C Virus Using Strand-Specific RT/PCR" Virol. 202, 606-614, 1994.
Lim et al. "Identification and Molecular Characterization of the Complete Genome of a Singapore Isolate of Hepatitis C Virus: Sequence Comparison with other Strains and Phylogenetic Analysis" Virus Genes 23, 89-95, 2001.
Pincus et al., "Treatment of HIV Tissue Culture Infection with Monoclonal Antibody-Ricin A Chain Conjugates" J. Immunol. 142, 3070-3075, 1989.
Steiger et al., "Competitive polymerase chain reaction assay for quantitation of HIV-1 DNA and RNA" J. Virol. Methods 34(2) 149-160, 1991.
Trowbridge, "Endocytosis and signals for internalization" Current Opinion in Cell Biology, 3, 634-641, 1991.
Vandamme et al, "Detection of HIV-1 RNA in plasma and serum samples using the NASBA amplification system compared to RNA-PCR" J. Virol. Methods 52(1-2) 121-132, 1995.
Yeh et al., "Quantitative assessment of hepatitis C virus RNA by polymerase chain reaction and a digoxigenin detection system: comparison with branched DNA assay" J. Virol. Methods 65(2) 219-226, 1997.
Bamezai et al., Internalization of Phosphotidylinositol-anchored Lymphocyte Proteins, *J Immunol.*, 143:3107-16, (1989).
Boyer et al., Comparison of Phosphorylation and Internalization of the Antigen Receptor/CD3 Complex, CD8, and Class I MHC-Encoded Proteins on T Cells, *J Immunol.* 143:1905-14, (1989).

(Continued)

*Primary Examiner*—Stacy B. Chen
(74) *Attorney, Agent, or Firm*—Foley & Lardner, LLP

(57) ABSTRACT

A chimeric transmembrane protein which promotes viral entry into cells comprises: (i) an extracellular domain capable of binding a virus; and (ii) an intracellular internalisation signal.

34 Claims, 13 Drawing Sheets

OTHER PUBLICATIONS

Ehrlich, et al., A single internalization signal from the di-leucine family is crtical for constitutive endocytosis of the type II TGF-β receptor, *J. Cell Science*, 114:1777-1786, (2001).

Fong & Le, The Processing of Ligands by the Class A Scavenger Receptor Is Dependent on Signal Information Located in the Cytoplasmic Domain, *J Biol Chem.*, 274:36808-16, (1999).

Hicke, L. et al., Cytoplasmic Tail Phosphorylation of the α-Factor Receptor Is Required for Its Ubiquitination and Internalization, *J. Cell Biology*, 141:349-358, (1998).

Kishi, H., & Ascoli, M., Multiple Distant Amino Acid Residues Present in the Serpentine Region of the Follitropin Receptor Modulate the Rate of Agonist-induced Internalization, *J. Biol. Chem.*, 275:31030-31037, (2000).

Kumar et al., Internalization of Interleukin 2 (IL-2) By High Affinity Il-2 Receptors is Required for the Growth of IL-2-Dependent T Cell Lines, *J Immunol.*, 139:3680-4, (1987).

Maestes, D.C., et al., Differential Phosphorylation Paradigms Dictate Desensitization and Internalization of the *N*-Formyl Peptide Receptor, *J. Biol. Chem.*, 274:29791-29795, (1999).

Mitchell et al., Cytoplasmic Tail Deletion Converts Membrane Immunoglobulin to a Phosphatidylinositol-linked Form Lacking Signaling and Efficient Antigen Internalization Functions, *J Biol Chem.* 266:8856-60, (1991).

Parent, J.-L. et al., Role of the Differentially Spliced Carboxyl Terminus in Thromboxane $A_2$ Receptor Trafficking, Identification of a Distinct Motif for Tonic Internalization, *J. Biol. Chem.*, 276:7079-7085, (2001).

Pisegna, J.R. et al., Essential Structural Motif in the C-Terminus of the PACAP Type I Receptor for Signal Transduction and Internalization, *Annals of the New York Academy of Sciences*, 921:195-201, (2000).

Prince et al., Efficient Endocytosis of the Cystic Fibrosis Transmembrane Conductance Regulator Requires a Tyrosine-based Signal, *J Biol Chem.*, 274:3602-9, (1999).

Stefan et al., The Third Cytoplasmic Loop of a Yeast G-Protein-Coupled Receptor Controls Pathway Activation, Ligand Discrimination, and Receptor Internalization, *Molecular and Cellular Biology*, 14:3339-3349, (1994).

Stitt et al., Advanced glycation end-product receptor interactions on microvascular cells occur within caveolin-rich membrane domains, *FASEB J.*, 14:2390-2, (2000).

Tan et al., The Sequence NPFXD Defines a New Class of Endocytosis Signal in *Saccharomyces cerivisiae*, *J Cell Biol.*, 135:1789-800, (1996).

Zwaaqstra et al., Transforming Growth Factor (TGF)-β1 Internalization—Modulation by Ligand Interaction with TGF-β Receptors Types I and II and a Mechanism that is Distinct From Clathrin-mediated Endocytosis, *J Biol Chem.*, 276:27237-45, (2001).

* cited by examiner (A)

Fig. 4
(A)
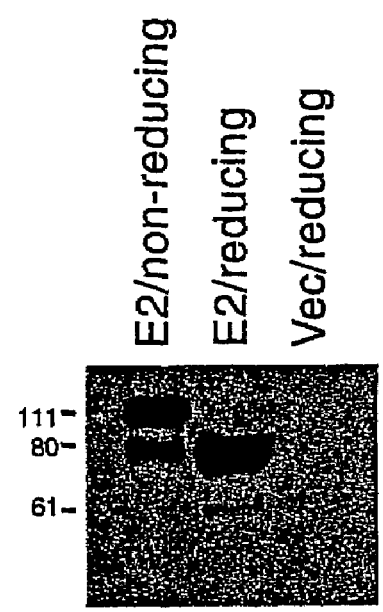
(B)
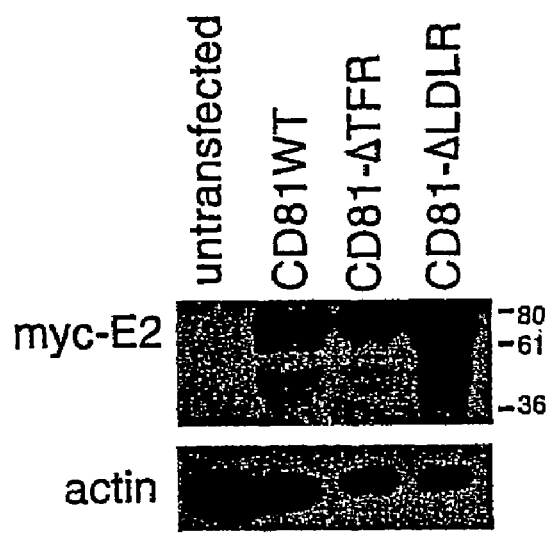

Fig. 7
(A)
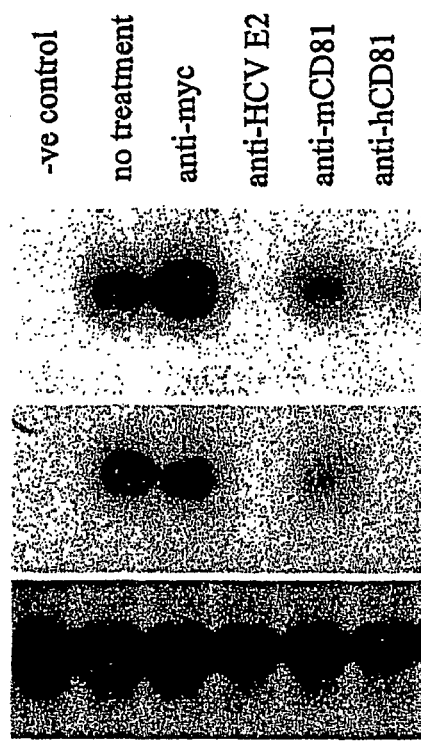
plus strand RNA (P1P5)
minus strand RNA (TAG/P4)
GAPDH
(B)
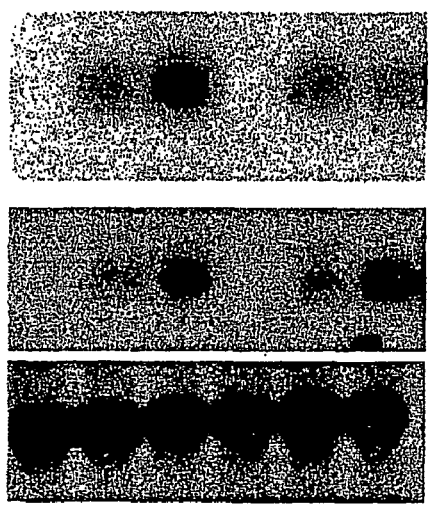
plus strand RNA (P1P5)
minus strand RNA (TAG/P4)
GAPDH

```
ATGCAGCTGGATATGTTCTTCCTGATGGCAGTGGTTATAGGGGTCAATTCAGAGGTTCAGTTGCAGCAGTCTGGGGCTGAACTTGTGAGG  90
 M  Q  L  D  M  F  F  L  M  A  V  V  I  G  V  N  S  E  V  Q  L  Q  Q  S  G  A  E  L  V  R

CCAGGGGCCTCAGTCAAGTTGTCCTGCACAGCTTCTGGCTTTAACATTAAAGACGACTATATGCACTGGGTGAAGCAGAGGCCTGAACAG  180
 P  G  A  S  V  K  L  S  C  T  A  S  G  F  N  I  K  D  D  Y  M  H  W  V  K  Q  R  P  E  Q

GGCCTGGAGTGGATTGGATGGATTGATCCTGAAAATGGTGATACTGAATATGCCTCGAAGTTCCAGGGCAAGGCCACAATAACACCAGAC  270
 G  L  E  W  I  G  W  I  D  P  E  N  G  D  T  E  Y  A  S  K  F  Q  G  K  A  T  I  T  P  D

ACATCCTCCAACACAGCCTACCTGCAGCTCAGCAGCCTGACATCTGAGGACACTGCCGTCTATTACTGTATTACAAGGGGTAACTGGGGC  360
 T  S  S  N  T  A  Y  L  Q  L  S  S  L  T  S  E  D  T  A  V  Y  Y  C  I  T  R  G  N  W  G

CAAGGCACCACTCTNACAGTCTCCTCAGCCAAAACGACACCCCCATCTGTCTATCCACTGGCCCTGGATCTGCTGCCCAAACTAACTCCA  450
 Q  G  T  T  L  T  V  S  S  A  K  T  T  P  P  S  V  Y  P  L  A  L  D  L  L  P  K  L  T  P
```

(B)

```
ATGAAGTTTCCTTCTCAACTTCTGCTCTTCCTGCTGTTCAGAATCACAGGCATAATATGTGACATCCAGATGACACAATCTTCATCCTAC  90
 M  K  F  P  S  Q  L  L  L  F  L  L  F  R  I  T  G  I  I  C  D  I  Q  M  T  Q  S  S  S  Y

TTGTCTGTATCTCTAGGAGGCAGAGTCACCATTACTTGCGAGGCAAGTGACCACATTAATAATTGGTTAGCCTGGTATCAGCAGAAACCA  180
 L  S  V  S  L  G  G  R  V  T  I  T  C  E  A  S  D  H  I  N  N  W  L  A  W  Y  Q  Q  K  P

GGAAATGCTCCTAGGCTCTTAATATCTGGTGCAACCACTTTGGAAACTGGGGTTCCTTCAAGATTCAGTGGCAGTGGATCTGGAAAAGAT  270
 G  N  A  P  R  L  L  I  S  G  A  T  T  L  E  T  G  V  P  S  R  F  S  G  S  G  S  G  K  D

TACACTCTCAGCATTACCAGTCTTCAGACTGAAGATGTTGCTACTTATTACTGTCAACAGTATTGGGAGTCCTCCGTACACGTTCGGAGG  360
 Y  T  L  S  I  T  S  L  Q  T  E  D  V  A  T  Y  Y  C  Q  Q  Y  W  E  S  S  V  H  V  R  R

GGGGACCAAGCTGGAAATAAAACGGGC  387
 G  D  Q  A  G  N  K  T  G
```

(A) 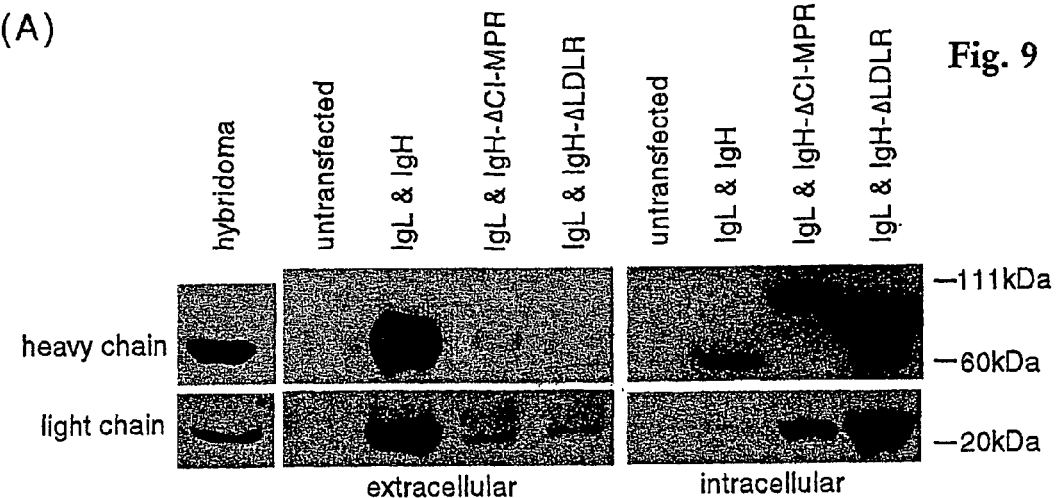
(B) 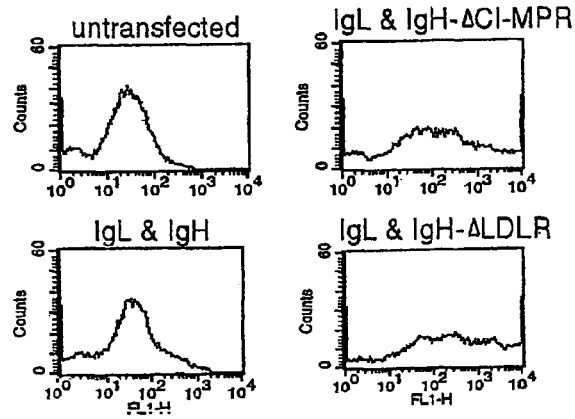
(C) 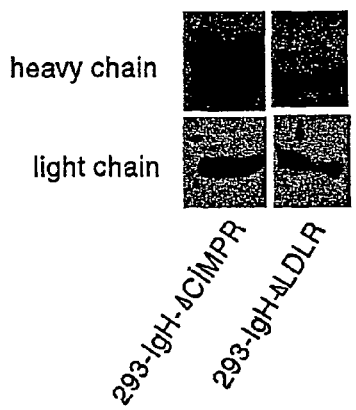
Fig. 9

Fig. 11
(A)
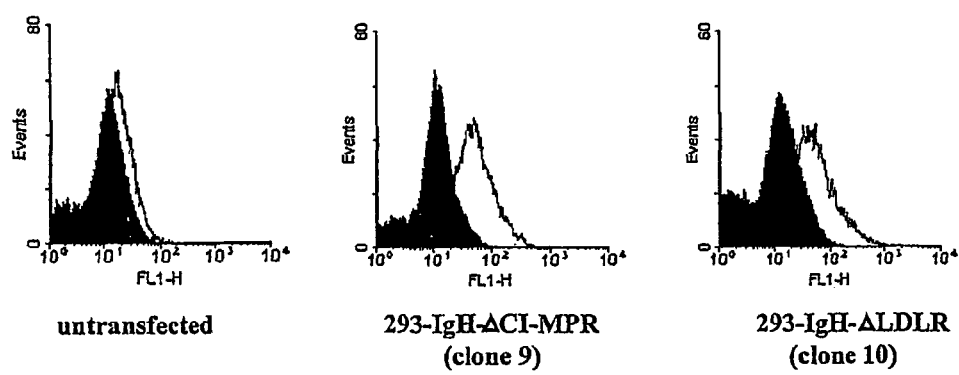
untransfected     293-IgH-ΔCI-MPR (clone 9)     293-IgH-ΔLDLR (clone 10)
(B)
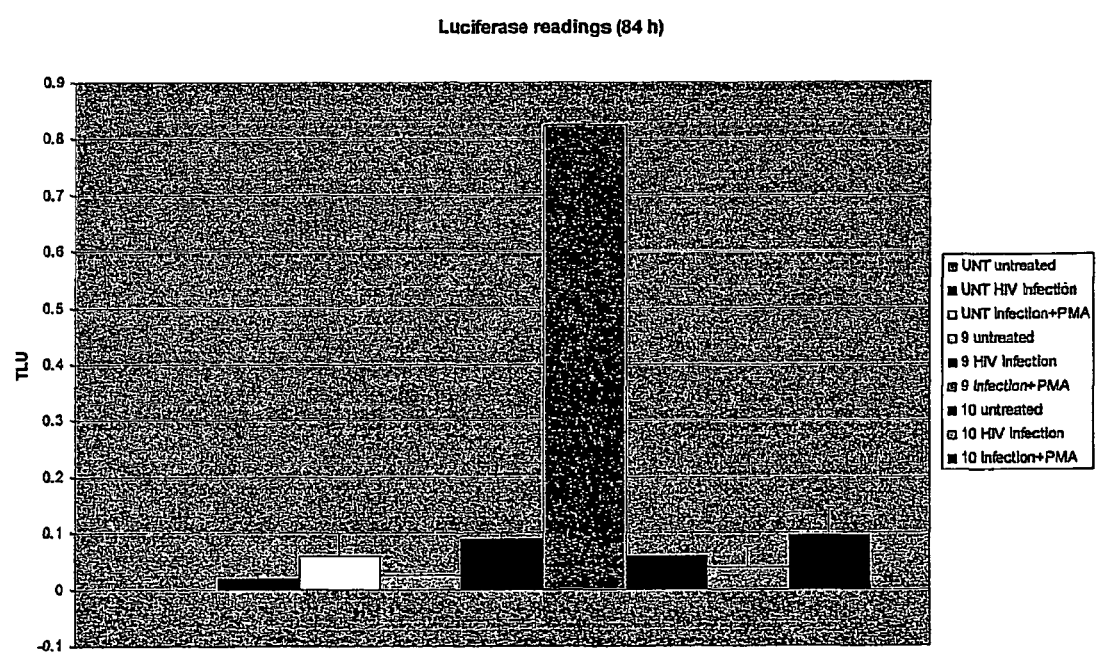

|  | untransfected | Huh7-CD81WT | Huh7-TfR-CD81 |  |
|---|---|---|---|---|
| I |  |  |  | positive strand |
| II |  |  |  | GAPDH |
| III |  |  |  | negative strand |
| IV |  |  |  | negative strand (Southern blot) |

(B)

| no treatment | | | 0.05% deoxychloate | | |
|---|---|---|---|---|---|
| untransfected | Huh7-CD81WT | Huh7-TfR-CD81 | untransfected | Huh7-CD81WT | Huh7-TfR-CD81 |

(C)

```
 74 CCATGGCGTTAGTATGAGTGTCGTGCAGCCTCCAGGACCCCCCCTCCCGGGAGAGCCATAGTGGTCTGCG HCV-BK
    ..................................................................... HCV-1
    ..................................................................... patient A
    ..................................................................... patient B 144 GAACCGGTGAGTACACCGGAATTGCCAGGACGACCGGGTCCTTTCTTGGATCAACCCGCTCAATGCCTGG HCV-BK
    ..................................................................... HCV-1
    ..................................................................... patient A
    ...............[?]................................................... patient B 214 AGATTTGGGCGTGCCCCCGCGAGACTGCTAGCCGAGTAGTGTTGGGTCGCGAAAGGCCTTGTGGT HCV-BK
    ................[?]............................................. HCV-1
    ................................................................ patient A
    ..............................[?]............................... patient B
```

Fig. 13
(A)
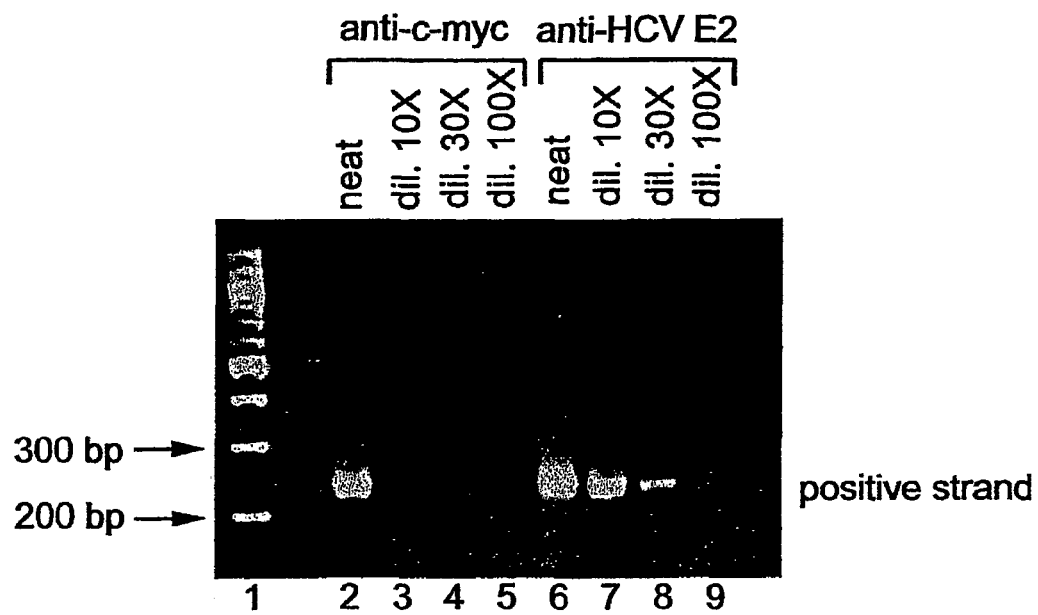
(B)
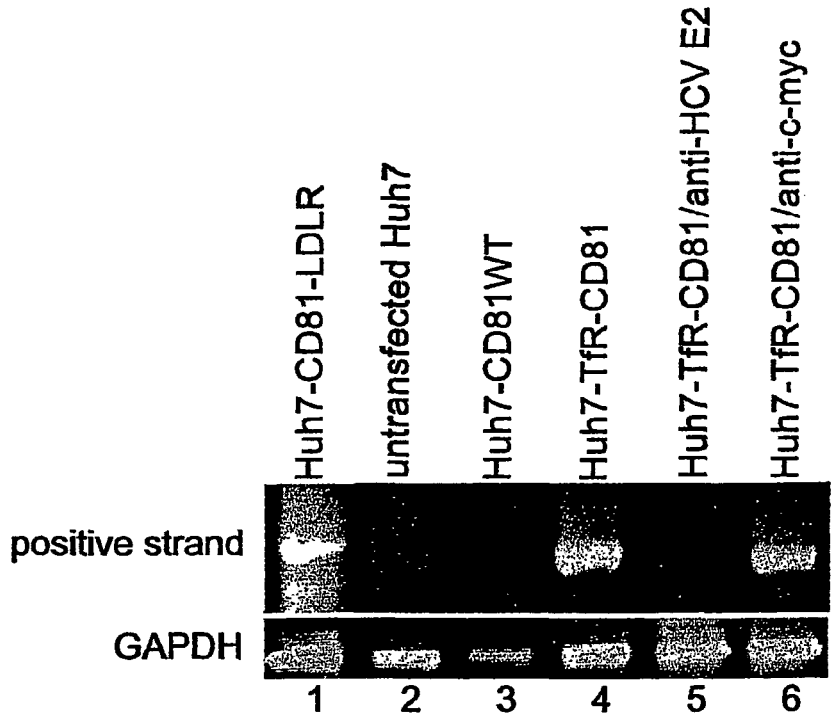

SEQUENCE LISTING

<160> NUMBER OF SEQ ID NOS: 42

<210> SEQ ID NO 1
<211> LENGTH: 55
<212> TYPE: DNA
<213> ORGANISM: Artificial Sequence
<220> FEATURE:
<223> OTHER INFORMATION: Description of Artificial Sequence: Synthetic Primer

<400> SEQUENCE: 1
aaagctagcg gatccgccac catgggagtg gagggctgca ccaagtgcat caagt        55

<210> SEQ ID NO 2
<211> LENGTH: 65
<212> TYPE: DNA
<213> ORGANISM: Artificial Sequence
<220> FEATURE:
<223> OTHER INFORMATION: Description of Artificial Sequence: Synthetic Primer

<400> SEQUENCE: 2
aaagaattcg cggccgctca gtacacggag ctgttccgga tgccacagca cagcaccatg    60
ctcag                                                                65

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Synthetic Primer

<400> SEQUENCE: 3
cccaagctta ccatggcgat gatggatcaa gctagatcag ca         42

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 4
cgcggatccc ctttttggtt ttgtgacatt ggc         33

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ccggaattca agaactggcg gcttaagaac atc         33

<210> SEQ ID NO 6
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
ataagaatgc ggccgctcac gccacgtcat cctccag         37

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
gggggatcca ccacacccaa gtgatggggg         30

<210> SEQ ID NO 8
<211> LENGTH: 31
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
ggggatatct ctctgatcta tccctgtcct c         31

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer -continued

```
<400> SEQUENCE: 9
actcattccc attctgcagc ttcc                                          24

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
ctgtgaggaa ctactgtct                                                19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
cggtgtactc accggttcc                                                19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
actcgcaagc accctatca                                                19

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 13
tcgcgaccca acactactc                                                19

<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
tcatggtggc gaataaactc attcccattc tgcagcttcc                         40

<210> SEQ ID NO 15
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
```
tcatggtggc gaataa                                                     16

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
gcagaaagcg tctagccatg gcgttagtat                                      30

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
accatgaagt ttccttctca acttctgctc ttcc                                 34

<210> SEQ ID NO 18
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
gcgccgtcta gaattaacac tcattcctgt tgaa                                 34

<210> SEQ ID NO 19
<211> LENGTH: 34
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 19
gggaattcat graatgsasc tgggtywtyc tctt                                 34

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 20
actagtcgac atggactcca ggctcaattt agtttttcct                           39

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 21
ttatttacca ggagagtggg agaggctctt                            30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 22
cccaagcttg cagtcggcgc ggtgctcagc                            30

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 23
ataagaatgc ggccgctcag atgtgtaaga ggtcctcgtc                 40

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 24
cccaagcttc tgtccattgt cctccccatc                            30

<210> SEQ ID NO 25
<211> LENGTH: 37
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 25
ataagaatgc ggccgctcac gccacgtcat cctccag                    37

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 26
atactcgagg tgcacggtct acgagacct                             29

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 27
ctgtgaggaa ctactgtctt                                       20

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 28
cactctcgag caccctatca ggcagt                                           26

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 29
ttcacgcaga aagcgtctag                                                  20

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 30
tcatggtggc gaataaactc caccatagat cactcc                                36

<210> SEQ ID NO 31
<211> LENGTH: 16
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 31
tcatggtggc gaataa                                                      16

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 32
gcagaaagcg tctagccatg gcgttagtat                                       30

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 33
ctgagaacgg gaagcttgtc atca                                             24

<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 34
cgtctagctc agggatgacc ttg                                          23

<210> SEQ ID NO 35
<211> LENGTH: 450
<212> TYPE: DNA
<213> ORGANISM: Artificial Sequence
<220> FEATURE:
<223> OTHER INFORMATION: Description of Artificial Sequence: Synthetic
      DNA from Hybridoma 902
<220> FEATURE:
<221> NAME/KEY: modified_base
<222> LOCATION: (375)
<223> OTHER INFORMATION: a, t, c or g
<220> FEATURE:
<221> NAME/KEY: CDS
<222> LOCATION: (1)..(450)

<400> SEQUENCE: 35

```
atg cag ctg gat atg ttc ttc ctg atg gca gtg gtt ata ggg gtc aat      48
Met Gln Leu Asp Met Phe Phe Leu Met Ala Val Val Ile Gly Val Asn
 1               5                  10                  15 tca gag gtt cag ttg cag cag tct ggg gct gaa ctt gtg agg cca ggg      96
Ser Glu Val Gln Leu Gln Gln Ser Gly Ala Glu Leu Val Arg Pro Gly
             20                  25                  30 gcc tca gtc aag ttg tcc tgc aca gct tct ggc ttt aac att aaa gac     144
Ala Ser Val Lys Leu Ser Cys Thr Ala Ser Gly Phe Asn Ile Lys Asp
         35                  40                  45 gac tat atg cac tgg gtg aag cag agg cct gaa cag ggc ctg gag tgg     192
Asp Tyr Met His Trp Val Lys Gln Arg Pro Glu Gln Gly Leu Glu Trp
     50                  55                  60 att gga tgg att gat cct gaa aat ggt gat act gaa tat gcc tcg aag     240
Ile Gly Trp Ile Asp Pro Glu Asn Gly Asp Thr Glu Tyr Ala Ser Lys
 65                  70                  75                  80 ttc cag ggc aag gcc aca ata aca cca gac aca tcc tcc aac aca gcc     288
Phe Gln Gly Lys Ala Thr Ile Thr Pro Asp Thr Ser Ser Asn Thr Ala
                 85                  90                  95 tac ctg cag ctc agc agc ctg aca tct gag gac act gcc gtc tat tac     336
Tyr Leu Gln Leu Ser Ser Leu Thr Ser Glu Asp Thr Ala Val Tyr Tyr
            100                 105                 110 tgt att aca agg ggt aac tgg ggc caa ggc acc act ctn aca gtc tcc     384
Cys Ile Thr Arg Gly Asn Trp Gly Gln Gly Thr Thr Leu Thr Val Ser
        115                 120                 125 tca gcc aaa acg aca ccc cca tct gtc tat cca ctg gcc ctg gat ctg     432
Ser Ala Lys Thr Thr Pro Pro Ser Val Tyr Pro Leu Ala Leu Asp Leu
    130                 135                 140 ctg ccc aaa cta act cca                                            450
Leu Pro Lys Leu Thr Pro
145                 150
```

<210> SEQ ID NO 36
<211> LENGTH: 150
<212> TYPE: PRT
<213> ORGANISM: Artificial Sequence
<220> FEATURE:
<223> OTHER INFORMATION: Description of Artificial Sequence: Synthetic
      IgH chain from Hybridoma 902

<400> SEQUENCE: 36

```
Met Gln Leu Asp Met Phe Phe Leu Met Ala Val Val Ile Gly Val Asn
 1               5                  10                  15

Ser Glu Val Gln Leu Gln Gln Ser Gly Ala Glu Leu Val Arg Pro Gly
             20                  25                  30

Ala Ser Val Lys Leu Ser Cys Thr Ala Ser Gly Phe Asn Ile Lys Asp
         35                  40                  45

Asp Tyr Met His Trp Val Lys Gln Arg Pro Glu Gln Gly Leu Glu Trp
     50                  55                  60

Ile Gly Trp Ile Asp Pro Glu Asn Gly Asp Thr Glu Tyr Ala Ser Lys
 65                  70                  75                  80

Phe Gln Gly Lys Ala Thr Ile Thr Pro Asp Thr Ser Ser Asn Thr Ala
                 85                  90                  95

Tyr Leu Gln Leu Ser Ser Leu Thr Ser Glu Asp Thr Ala Val Tyr Tyr
             100                 105                 110

Cys Ile Thr Arg Gly Asn Trp Gly Gln Gly Thr Thr Leu Thr Val Ser
         115                 120                 125

Ser Ala Lys Thr Thr Pro Pro Ser Val Tyr Pro Leu Ala Leu Asp Leu
     130                 135                 140

Leu Pro Lys Leu Thr Pro
145                 150
```

<210> SEQ ID NO 37
<211> LENGTH: 387
<212> TYPE: DNA
<213> ORGANISM: Artificial Sequence
<220> FEATURE:
<223> OTHER INFORMATION: Description of Artificial Sequence: Synthetic DNA from Hybridoma 902
<220> FEATURE:
<221> NAME/KEY: CDS
<222> LOCATION: (1)..(387)

<400> SEQUENCE: 37

```
atg aag ttt cct tct caa ctt ctg ctc ttc ctg ctg ttc aga atc aca      48
Met Lys Phe Pro Ser Gln Leu Leu Leu Phe Leu Leu Phe Arg Ile Thr
 1               5                  10                  15 ggc ata ata tgt gac atc cag atg aca caa tct tca tcc tac ttg tct      96
Gly Ile Ile Cys Asp Ile Gln Met Thr Gln Ser Ser Ser Tyr Leu Ser
             20                  25                  30 gta tct cta gga ggc aga gtc acc att act tgc gag gca agt gac cac     144
Val Ser Leu Gly Gly Arg Val Thr Ile Thr Cys Glu Ala Ser Asp His
         35                  40                  45 att aat aat tgg tta gcc tgg tat cag cag aaa cca gga aat gct cct     192
Ile Asn Asn Trp Leu Ala Trp Tyr Gln Gln Lys Pro Gly Asn Ala Pro
     50                  55                  60 agg ctc tta ata tct ggt gca acc act ttg gaa act ggg gtt cct tca     240
Arg Leu Leu Ile Ser Gly Ala Thr Thr Leu Glu Thr Gly Val Pro Ser
 65                  70                  75                  80 aga ttc agt ggc agt gga tct gga aaa gat tac act ctc agc att acc     288
Arg Phe Ser Gly Ser Gly Ser Gly Lys Asp Tyr Thr Leu Ser Ile Thr
                 85                  90                  95 agt ctt cag act gaa gat gtt gct act tat tac tgt caa cag tat tgg     336
Ser Leu Gln Thr Glu Asp Val Ala Thr Tyr Tyr Cys Gln Gln Tyr Trp
             100                 105                 110 gag tcc tcc gta cac gtt cgg agg ggg gac caa gct gga aat aaa acg     384
Glu Ser Ser Val His Val Arg Arg Gly Asp Gln Ala Gly Asn Lys Thr
         115                 120                 125
```

-continued

```
ggc                                                                      387
Gly <210> SEQ ID NO 38
<211> LENGTH: 129
<212> TYPE: PRT
<213> ORGANISM: Artificial Sequence
<220> FEATURE:
<223> OTHER INFORMATION: Description of Artificial Sequence: Synthetic
      IgL chain from Hybridoma 902

<400> SEQUENCE: 38

Met Lys Phe Pro Ser Gln Leu Leu Leu Phe Leu Leu Phe Arg Ile Thr
 1               5                  10                  15

Gly Ile Ile Cys Asp Ile Gln Met Thr Gln Ser Ser Ser Tyr Leu Ser
            20                  25                  30

Val Ser Leu Gly Gly Arg Val Thr Ile Thr Cys Glu Ala Ser Asp His
        35                  40                  45

Ile Asn Asn Trp Leu Ala Trp Tyr Gln Gln Lys Pro Gly Asn Ala Pro
    50                  55                  60

Arg Leu Leu Ile Ser Gly Ala Thr Thr Leu Glu Thr Gly Val Pro Ser
65                  70                  75                  80

Arg Phe Ser Gly Ser Gly Ser Gly Lys Asp Tyr Thr Leu Ser Ile Thr
                85                  90                  95

Ser Leu Gln Thr Glu Asp Val Ala Thr Tyr Tyr Cys Gln Gln Tyr Trp
            100                 105                 110

Glu Ser Ser Val His Val Arg Arg Gly Asp Gln Ala Gly Asn Lys Thr
        115                 120                 125

Gly

<210> SEQ ID NO 39
<211> LENGTH: 205
<212> TYPE: DNA
<213> ORGANISM: Hepatitis C virus

<400> SEQUENCE: 39
ccatggcgtt agtatgagtg tcgtgcagcc tccaggaccc ccctcccgg gagagccata      60 gtggtctgcg aaccggtga gtacaccgga attgccagga cgaccgggtc ctttcttgga    120
tcaacccgct caatgcctgg agatttgggc gtgcccccgc gagactgcta gccgagtagt    180
gttgggtcgc gaaaggcctt gtggt                                          205

<210> SEQ ID NO 40
<211> LENGTH: 205
<212> TYPE: DNA
<213> ORGANISM: Hepatitis C virus

<400> SEQUENCE: 40
ccatggcgtt agtatgagtg tcgtgcagcc tccaggaccc ccctcccgg gagagccata      60 gtggtctgcg aaccggtga gtacaccgga attgccagga cgaccgggtc ctttcttgga    120
tcaacccgct caatgcctgg agatttgggc gtgcccccgc aagactgcta gccgagtagt    180
gttgggtcgc gaaaggcctt gtggt                                          205

<210> SEQ ID NO 41
<211> LENGTH: 205
<212> TYPE: DNA
<213> ORGANISM: Homo sapiens

<400> SEQUENCE: 41
```

```
ccatggcgtt agtatgagtg tcgtgcagcc tccaggaccc ccctcccgg gagagccata      60 gtggtctgcg aaccggtga gtacaccgga attgccagga cgaccgggtc ctttcttgga     120
tcaacccgct caatgcctgg agatttgggc gtgccccgc gagactgcta gccgagtagt    180
gttgggtcgc gaaaggcctt gtggt                                          205

<210> SEQ ID NO 42
<211> LENGTH: 205
<212> TYPE: DNA
<213> ORGANISM: Homo sapiens

<400> SEQUENCE: 42
ccatggcgtt agtatgagtg tcgtgcagcc tccaggaccc ccctcccgg gagagccata      60 gtggtctgcg aaccggtga gtataccgga attgccagga cgaccgggtc ctttcttgga    120
tcaacccgct caatgcctgg agatttgggc gtgccccgc gagactacta gccgagtagt    180
gttgggtcgc gaaaggcctt gtggt                                          205
```

INTERNALISATION OF VIRUS INTO CELLS

FIELD OF THE INVENTION

The present invention relates to viral infection. In particular the invention relates to a protein designed to promote viral entry into cells, cells and a non-human transgenic animal comprising such a protein and a method of infecting such cells and animals with a virus. The invention also relates to methods for testing and screening anti-viral agents.

BACKGROUND OF THE INVENTION

In order for a virus to establish an infection, it must first enter a cell. Human immunodeficiency virus type 1 (HIV-1) infection, for example, involves binding of the viral envelope protein gp120/160 to cell surface CD4 molecules followed by interactions with a coreceptor. This results in fusion of the viral and cellular membranes. HIV-1 virus uptake can be reconstituted in heterologous cell lines by the co-expression of CD4 and the respective chemokine receptor, suggesting that cell-type and species specific infection is largely determined at the level mediated by the viral receptors.

The mechanisms by which other viruses enter cells are less well understood and no proper cell-based systems are available. For example, hepatitis C virus (HCV) is thought to bind to CD81 receptors expressed on the cell surface of hepatocytes via the structural protein E2, although the role of CD81 in mediating viral entry is controversial as CD81 is widely expressed on cell surfaces and thus, cannot explain virus tropism to hepatocytes. Moreover, in cell fusion assays that use chimeric HCV envelope proteins, over-expression of human CD81 has been shown not to affect cell fusion activity. For many viruses, the cellular receptors are even less well characterized.

The process of receptor-mediated endocytosis, by which cells internalize their plasma membrane together with molecules bound to cell surface receptors, have been implicated as the route of cell entry by several viruses including rabies, herpes, Semliki Forest, African swine fever and HIV viruses. However, it has been reported that CD81 has a poor internalization efficiency and this may be one of the reasons why CD81-overexpressing cells are only moderately permissive and can not be reproducibly infected by HCV.

Constitutively cycling receptors such as the transferrin receptor (TFR) and low density lipoprotein receptor (LDLR) are constitutively clustered in coated pits and can be rapidly internalized, transported to the acidic endosome and finally recycled back to the cell surface. The constitutive internalisation of such receptors is mediated by internalisation signals in their cytoplasmic domains. These internalisation signals are self-determined structural motifs that may confer recycling properties to proteins that are not normally endocytosed.

SUMMARY OF THE INVENTION

The present invention is based on the finding that a chimeric protein comprising an extracellular domain capable of binding to a virus and an intracellular internalisation domain enables virus to enter cells in which it is expressed and thus enables viral infection to be established. In particular, the present inventors have engineered endocytosis and membrane anchoring signals into the C-terminus of the immunoglobulin heavy chain and have shown that these chimeric antibodies are displayed on the cell surface and undergo endocytosis. The inventors have shown that these cell surface antibodies can bind HIV-1 virus with high affinity which binding results in the internalization of the virus into a human kidney cell line.

In addition, the present inventors have constructed two CD81 chimeric receptors by linking either the N or C-terminus of CD81 with cytoplasmic domains of the transferrin receptor (TFR) or the low density lipoprotein receptor (LDLR), respectively and have found that the CD81 chimeras have better internalization efficiency than wild-type CD81. Further, the inventors have shown that the internalization efficiencies of these receptors is correlated with infectivity of cultured liver cells that are over-expressing either wild-type or chimeric CD81 receptors by HCV virions produced by a tetracycline-inducible cell culture system.

Cells and non-human transgenic animals expressing such chimeric proteins are useful in methods for identifying novel pharmaceutical agents. These agents may be used in the therapeutic and/or prophylactic treatment of viral infections.

Accordingly, the present invention provides:
  a chimeric transmembrane protein comprising:
    (i) an extracellular domain capable of binding a virus; and
    (ii) an intracellular internalisation signal;
  a polynucleotide encoding a protein of the invention;
  a vector comprising a polynucleotide of the invention;
  a cell comprising a protein, polynucleotide or vector of the invention;
  a cell comprising a protein of the invention, which cell is infected with a virus that is capable of binding to said protein;
  a transgenic non-human animal comprising a cell of the invention;
  a method for identifying an anti-viral agent, said method comprising:
    (i) providing a cell expressing a protein of the invention or a non-human transgenic animal comprising a cell expressing a protein of the invention, which cell or animal is infected with a virus;
    (ii) contacting said cell or animal with a test agent; and
    (iii) monitoring viral infection;
  thereby determining whether the test agent has anti-viral activity;
  a method for identifying an anti-viral vaccine or agent capable of preventing or inhibiting viral infection, which method comprises:
    (i) providing a cell expressing a protein of the invention or a non-human transgenic animal comprising a cell expressing a protein of the invention;
    (ii) contacting said cell or animal with a test agent;
    (iii) contacting said cell or animal with a virus capable of binding to said protein; and
    (iv) determining whether the test agent prevents or limits viral infection.

BRIEF DESCRIPTION OF THE DRAWINGS

FIG. 4A shows that under non-reducing conditions, E2 exists mainly as high molecular weight aggregates with only a small percentage existing as monomers. In the presence of reducing agent, all aggregates dissociated to form monomers. Truncated E2 protein was expressed in 293T cells and detected using an anti-myc antibody as the protein was fused to a myc-tag at the C-terminal. Control cells were transfected with vector only.

FIG. 4B illustrates the binding of truncated E2 protein to Huh7 stable clones overexpressing wild-type or chimeric CD81 which was observed after E2 protein was overlaid onto monolayers of cells at 37° C. for 4 h. No binding of E2 to untransfected Huh7 cells was observed. Beta-actin expression showed equal loading of total cell lysate.

FIG. 7A shows the results of viral infection experiments. Lanes 2 to 4: No viral transcripts were observed in Huh7-CD81WT cells overlaid with infectious media that has been pre-cleared with an anti-E2 antibody, while viral transcripts were observed when the cells were overlaid with infectious media not pre-cleared or pre-cleared with control anti-c-myc antibody. Lanes 5 and 6: No viral transcripts were observed in Huh7-CD81WT cells when the cells were pre-incubated with an anti-human CD81 antibody (anti-hCD81) before the addition of infectious media. On the other hand, pre-incubation with an anti-mouse CD81 antibody (anti-mCD81) did not affect the infection of Huh7-CD81WT cells. A negative control was performed using cells that were overlaid with non-infectious media.

FIG. 7B shows the results of blocking experiments performed on Huh7-CD81-ΔTFR cells. Pre-clearing with anti-E2 prevented infection (lane 2 to 4). However, infection of Huh7-CD81-ΔTFR was not blocked by anti-human CD81 antibody (lane 5) presumably because of the higher internalization efficiency of CD81-ΔTFR chimeric receptor compared to wild-type CD81.

FIG. 8 shows the partial sequences of IgH (A) (SEQ ID NOs:35-36) and IgL (B) (SEQ ID NOs:37-38) chains isolated from hybridoma 902 showing the open reading frame and the variable regions. N-terminal sequences of the mature proteins determined by Edman sequencing are underlined.

FIG. 9A shows the results of western analysis indicating that IgH and IgL associated with each other. Culture medium (containing secreted/extracellular proteins) and cell lysate (intracellular protein released by cell lysis) from transiently transfected cells were incubated with protein A/G beads and bound IgH and IgL were detected by western analysis. Cells transfected with IgL and IgH secreted both chains into the culture medium and they were associated with each other since capturing IgH with protein A/G beads also pulled down IgL proteins. For cells transfected with IgL and chimeric IgH (IgH-ΔCI-M6PR or IgH-ΔLDLR), the heavy chains were found intracellularly, indicating that they were associated with the membranes.

FIG. 9B shows the results of FACScan analysis illustrating that cells transiently transfected with IgL and IgH did not express antibody on the cell surface, as the mean fluorescence of the cells was the same as untransfected cells. In contrast, cells transfected with IgL and chimeric IgH (IgH-ΔCI-M6PR or IgH-ΔLDLR) showed high mean fluorescence, indicating that the antibodies were expressed on the cell surface.

FIG. 9C shows the expression of heavy and light chain antibodies in cell lysates of stable clones of 293 cells transfected with IgL and IgH-ΔCI-M6PR or IgH-ΔLDLR.

FIG. 11A shows the expression of chimeric antibodies on the cell surfaces of stable clones of 293 cells transfected with IgL and IgH-ΔCI-M6PR (clone 9) or IgH-ΔLDLR (clone 10) as determined by FACScan analysis using an anti-mouse FITC-conjugated F(ab')$_2$ antibody (unfilled histograms). Filled histograms represented unstained cells. Untransfected cells were used as control.

FIG. 11B shows PMA-induction of luciferase activities in stably transfected 293-IgH-ΔCI-MPR (clone 9) cells after infection with the pseudotype-virus, HIV strain HBX2 (He and Landau, J.Virol. 69, 4587-4592, 1995), which contains a luciferase reporter gene inserted into the nef gene. Infected 293-IgH-ΔCI-MPR cells that were not treated with PMA did not show luciferase activity. Neither untransfected (UNT) nor 293-IgH-ΔLDLR (clone 10) cells showed significant luciferase activity.

FIG. 12 shows the internalization and replication of HCV in Huh7-TfR-CD81 cells. Nested RT-PCR was performed to assay for the presence of viral transcripts in Huh7 stables clones after they were exposed to sera from two HCV-infected patients (A and B). Cellular GAPDH mRNA was used to check that similar number of cells was used in the experiments (panel II). (A) After the cells were exposed to serum from patient A, a significant amount of positive strand HCV RNA was detected in Huh7-TfR-CD81 cells but not in untransfected Huh7 and Huh7-CD81WT cells (panel I, positive strand RT-PCR products visualized under UV light after ethidium bromide staining). Negative strand HCV RNA was also detected only in Huh7-TfR-CD81 cells (negative strand RT-PCR products visualized under UV light after ethidium bromide staining panel (III) and analyzed by Southern blot with a specific probe (panel IV)). (B) No positive or negative strand viral transcripts were detected in untransfected Huh7, Huh7-CD81WT or Huh7-TfR-CD81 cells when serum from patient B was used directly to overlay onto the cells (without treatment, lanes 1-3, panel I, III and IV). When the serum was pre-treated with 0.05% deoxycholate before overlaying on the cells, positive strand RT-PCR products was observed in Huh7-TfR-CD81 but not in untransfected Huh7 and Huh7-CD81WT cells (0.05% deoxychloate, lanes 4-6, panel I). Negative strand RT-PCR can be detected under UV light after ethidium bromide staining (panel III) and by Southern blot analysis (panel IV), only for Huh7-TfR-CD81 cells. (C) Positive strand RT-PCR products from Huh7-TfR-CD81 cells that were overlaid with the serum from patient A or B, were ligated into pCRII-TOPO vector and sequenced from both directions. Sequences (SEQ ID NOs:39-42, respectively, in order of appearance) were aligned and compared with the corresponding 5' non-coding region from representative isolates, HCV-BK for genotype 1b (Takamizawa et al, J. Virol 65, 1105-1113, 1991; GenBank accession number M58335) and HCV-1 for genotype 1a (Choo et al., PNAS USA 88, 2451-2455, 1991; GenBank accession number M62321). Nucleotides matching to HCV-BK are represented by and mismatches are boxed. Nucleotide numberings shown on the left refer to the nucleotide positions in HCV-BK.

FIG. 13 shows that internalization of HCV particles was abolished when patient serum was pre-cleared with an anti-HCV E2 antibody. After the overlay experiments shown in FIG. 12A, the remaining serum from patient A was refrozen at −80° C. and later, thawed again for these experiments. (A) Serum was immunoprecipitated with an anti-HCV E2 antibody or anti-c-myc antibody (negative control) and protein A/G beads. After washing, RNA was extracted from the immuno-complexes and analyzed at different dilutions for the presence of positive strand HCV RNA. Some HCV RNA were immunoprecipitated by both antibodies (neat, lanes 2 and 6) but significantly (10-30×) more HCV RNA were bound to anti-E2 antibody (lanes 6 to 9) than anti-c-myc antibody (lanes 2 to 5). RT-PCR products were still detected when the RNA immunoprecipitated by anti-E2 antibody was diluted 10× and 30× but no RT-PCR products observed for anti-c-myc antibody at these dilutions. DNA marker was loaded in lane 1 (bp represents base pairs). (B) RT-PCR was performed to assay for the presence of positive strand viral transcripts in Huh7 stables clones after they were exposed to serum from patients A. Positive strand RT-PCR products were observed in Huh7-TfR-CD81 (lane 4) and Huh7-CD81-LDLR (lane 1) cells but not in untransfected Huh7 (lane 2) or Huh7-CD81WT cells (lane 3). No positive strand RT-PCR products was observed in Huh7-TfR-CD81 cells overlaid with serum that was pre-cleared with an anti-HCV E2 antibody (lane 5), while positive strand RT-PCR products were observed when the cells were overlaid with serum that was pre-cleared with control anti-c-myc antibody (lane 6).

DETAILED DESCRIPTION OF THE INVENTION

Figure 1:
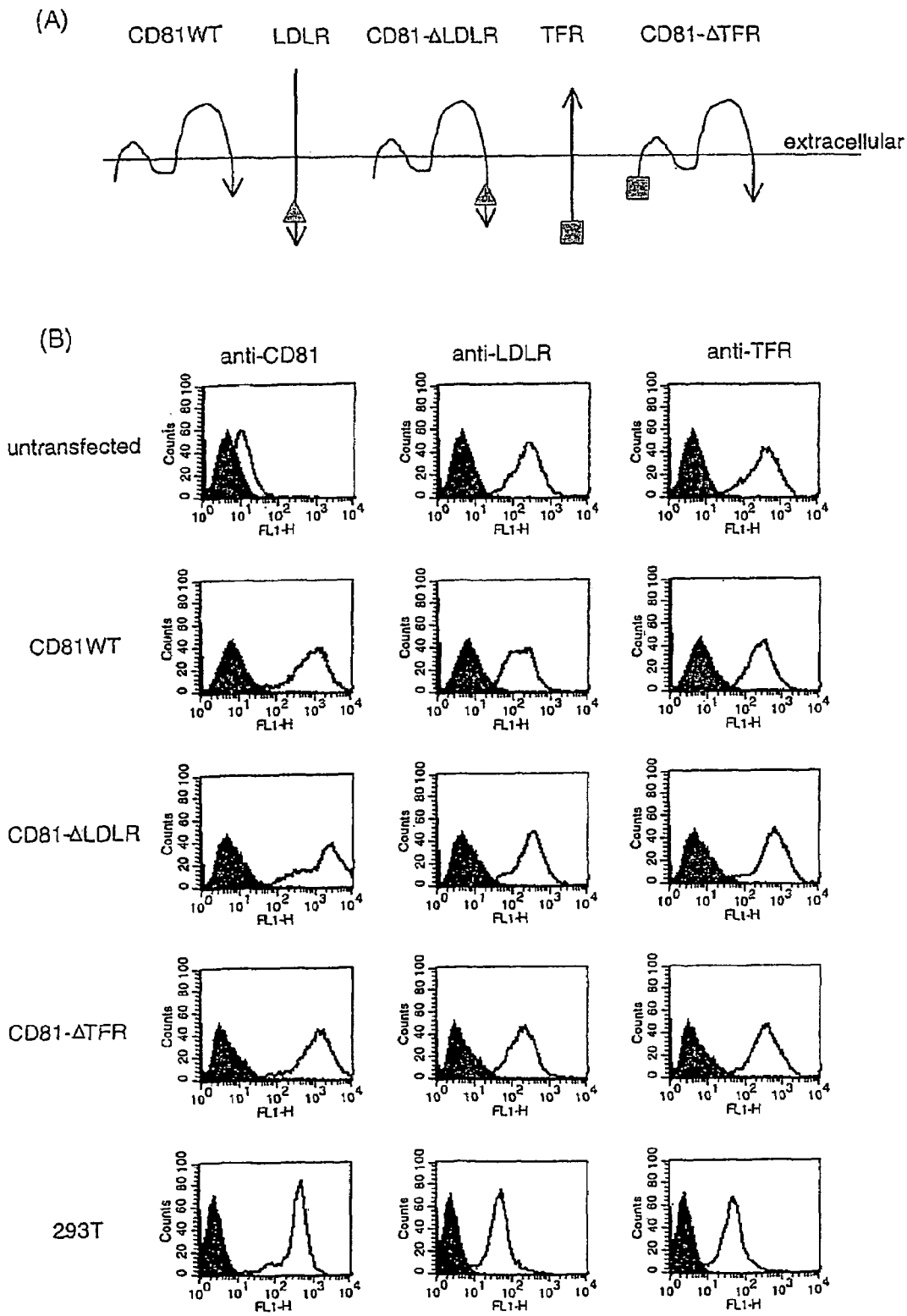
FIG. 1A is a schematic diagram showing the membrane topologies of wild-type CD81, transferrin receptors (TFR) and low density lipoprotein receptors (LDLR), and the predicted topologies of CD81 chimeras. σ and ν represent cytoplasmic domains of LDLR and TFR, respectively, that were fused to CD81 to form chimeric receptors.
FIG. 1B shows the results of FACScan analysis of the surface expression of CD81, transferrin and LDL receptors in parental Huh7 and stably transfected Huh7 clones. Cells were stained with specific antibodies (anti-CD81, anti-TFR or anti-LDLR), followed by phycoerythrin-conjugated goat anti-mouse IgG (unfilled histograms). Filled histograms represented staining by phycoerythrin-conjugated antibody only. 293T cells expressing endogenous receptors were used as positive controls.

The present invention provides a chimeric transmembrane protein comprising or, in some embodiments, consisting essentially of:
(i) an extracellular domain capable of binding a virus; and
(ii) an intracellular internalisation signal.

The protein may comprise a single polypeptide or may comprise two or more associated polypeptides. Preferably, the protein comprises a single polypeptide or two associated polypeptides.

Where the protein comprises two or more polypeptides, one or more of the polypeptides may comprise a transmembrane domain. The extracellular domain and the intracellular internalisation signal may be part of the same polypeptide or may be present on associated polypeptides. Association of two or more polypeptides typically results in the constitutive internalisation of all associated polypeptides.

Extracellular Domain

An extracellular domain is capable of binding a virus. The virus may be a DNA virus or a RNA virus. It may be a single-stranded virus or a double-stranded virus. The virus may be a flovivirus, picomavirus, myxovirus or herpes virus.

Typically binding of the extracellular domain to a virus occurs by interaction of the extracellular domain with a viral protein. Generally, this viral protein will be expressed on the cell-surface of the virus. For example, where the virus is HIV the extracellular domain of the protein is typically capable of binding to gp120/160. Where the virus is HCV, the extracellular domain is typically capable to binding to E2. Where the virus is influenza A virus, the extracellular domain is typically capable of binding to hemagglutinin. Where the virus is herpes simplex virus, the extracellular domain is typically capable of binding to glycoprotein C. Where the virus is a rhinovirus, the extracellular domain is typically capable of binding to external proteins VPs. Where the virus is Epstein-Barr virus, the extracellular domain is typically capable of binding to glycoprotein gp350.

The ability of the extracellular domain to bind to a virus can be determined using any suitable assay. Typically, the ability of the extracellular domain to bind to a virus will be determined by monitoring binding of the extracellular domain to a viral protein. Numerous methods for monitoring protein/protein interactions are known in the art, such as a co-precipitation, co-purification and overlay assays.

The extracellular domain may comprise an antibody, or a fragment thereof. Preferably, the extracellular domain comprises a fragment of an antibody, which fragment is capable of specifically binding to a viral protein. An antibody, or other protein, "specifically binds" to a protein when it binds with preferential or high affinity to the protein for which it is specific but does not substantially bind, not bind, or binds with only low affinity to other proteins. A variety of protocols for competitive binding or immunoradiometric assays to determine the specific binding capability of an antibody are well know in the art (see for example Maddox et al, J. Exp. Med. 158,1211-1226, 1993). Such immonoassays typically involve the formation of complexes between the specific protein and its antibody and the measurement of complex formation. Suitable antibody fragments include Fv, Fab and Fab' fragments and single-chain antibodies.

Preferably the antibody fragment capable of binding to a virus comprises a variable region of a heavy chain and a variable region of a light chain. Typically the heavy and light chains are associated such that they form a binding site for a viral protein.

Preferably the heavy chain fragment is fused to a transmembrane domain. Typically, the light chain fragment has no transmembrane domain and is associated with the heavy chain via non-covalent protein-protein interactions. Generally, the heavy chain and light chain will be associated by means of a disulphide bond. It is therefore preferred that the fragments of the light and heavy chains both contain one or more cysteine residues that form disulphide bonds in the whole antibody molecule.

The extracellular domain may comprise a cell surface receptor or a fragment thereof capable of binding to a virus. Any cell surface protein which recognises and binds to a virus, preferably to a specific protein on the surface of the virus may form the extracellular domain. For example where the virus is HIV the cell surface receptor is CD4 and where the virus is HCV the cell surface receptor is CD81, where the virus is influenza A virus the receptor is sialic acid, where the virus in Herpes simplex virus the receptor is glycosaminoglycan heparan sulphate, where the virus is Rhinovirus the receptor is ICAM-1 and where the virus is Epstein-Barr virus the receptor is C3d. A protein of the invention may comprise-intracellular and transmembrane regions from a cell surface receptor in addition to extracellular regions from the receptor.

Intracellular Domain

A transmembrane protein of the invention comprises an extracellular internalisation signal. The term internalisation signal refers to a region of a polypeptide which interacts with the endocytotic machinery in a cell such that a protein comprising this polypeptide region is constitutively internalised by endocytosis when present on the cell surface. A protein comprising an internalisation signal is typically constitutively recycled between the endocytic compartment and the cell surface.

An internalisation signal typically comprises a 4 or 6 residue internalisation motif in which the chemical and spatial pattern of critical residues is consistent with tight turn structure. Such motifs typically contain an aromatic amino-terminal residue and either an aromatic or large hydrophobic carboxy-terminal residue. Such signals are well known in the art, for example in Collawn (1991) EMBO J.10,3247-3253 and Trowbridge (1991) Current Opinion in Cell Biology, 3, 634-641.

The intracellular internalisation signal is typically a signal from a constitutively recycled receptor. Such receptors include a low density lipoprotein receptor (LDLR), the transferin receptor (TFR), a cation-dependent mannose-6-phosphate receptor (CD-Man-6-PR), a cation-independent mannose-6-phosphate receptor (CI-Man-6-PR), the poly Ig receptor and the asialo glycoprotein receptor (ASGPR).

The intracellular domain of a protein of the invention may comprise the entire intracellular domain of a constitutively recycling receptor or a fragment thereof. The transmembrane region of a protein of the invention may also be derived from a constitutively recycling receptor. A fragment of a constitutively recycling receptor typically comprises at least one internalisation signal. Preferably the fragment is from 4 to 40 amino acids in length, for example, from 5, 6, 7, 8, 9 or 10 to 20, 25, 30 or 35 amino acids.

The intracellular domain of a protein of the invention may comprise a fragment of a first constitutively recycling receptor and a fragment of a second constitutively recycling receptor. Such a chimeric intracellular domain will typically contain at least one internalisation signal from each recycling receptor.

Internalisation of a protein of the invention may be determined, for example, by exposing the surface of a cell expressing the protein to an antibody, virus or other molecule which binds to the extracellular domain of the protein, incubating the cell with the extracellular antibody or virus, washing to remove surface bound antibody or virus and determining the amount of internalised anitbody or virus. Typically, after a 1 hour incubation more than 30%, for example more than 40%, more than 50% or more than 60% of the protein is internalised. Preferably more than 70%, for example more than 80% or more than 90% of the protein is internalised after 1 hour.

Polynucleotide

The invention also provides a polynucleotide encoding a protein of the invention. The polynucleotide may be RNA or DNA. Preferably the polynucleotide is DNA. The polynucleotide is typically isolated. A polynucleotide according to the invention has utility in production of a protein of the invention.

The present invention also includes expression vectors that comprise a polynucleotide encoding a protein of the invention. Such expression vectors are routinely constructed in the art of molecular biology and may, for example, involve the use of plasmid DNA and appropriate initiators, promoters, enhancers and other elements, such as for example polyadenylation signals which may be necessary, and which are positioned in the correct orientation, in order to allow for protein expression. By way of further example in this regard we refer to Sambrook et al, 1989, Molecular Cloning: A Laboratory Manual, $2^{nd}$ Edition, CSH Laboratory Press.

Preferably a polynucleotide of the invention in a vector is operably linked to a control sequence which is capable of providing for the expression of the coding sequence by the host cell. The term "operably linked" refers to a juxta position wherein the components described are in a relationship permitting them to function in their intended manner. A regulatory sequence, such as a promoter, "operably linked" to a coding sequence is positioned in such a way that expression of the coding sequence is achieved under conditions compatible with the regulatory sequence.

The vectors may be for example, plasmid, virus or phage vectors provided with an origin of replication, optionally a promoter for the expression of the said polynucleotide and optionally a regulator of the promoter. The vectors may contain one or more selectable marker genes, for example an antibiotic resistance gene in the case of bacterial plasmid. Vectors may be used in vitro; for example for the production of DNA or RNA or used to transfect or transform a host cell, for example, in a mammalian host cell.

Promoters and other expression regulation signals may be selected to be compatible with the host cell for which expression is designed. Preferably the host cell is a mammalian cell. Mammalian promoters, such as β-actin promoters, may be used. Tissue-specific promoters are preferred. Viral promoters, which are readily available in the art, may also be used. For example, the Moloney Murine Leukemia Viral Long Terminal repeat (MMLV LTR), the Rous Sarcoma Virus (RSV) LTR promoter, the SV40 promoter, the human cytomegalovirus (CMV) IE promoter and HSV promoters.

Cells

The invention also include cells that have been modified to express a protein of the invention. The cells are typically provided in vitro. A culture of cells may be provided. Such cells are preferably mammalian cells, such as mouse cells, human cells or other primate cells. Particular examples of cells which may be modified by insertion of vectors encoding for a polypeptide of the invention into mammalian HEK293, HEK293T, CHO, Heta, BHK, 323, COS, Huh7, HepG2 and U937 cells. A cell line may be transiently transfected or is preferably stably transfected. Generally, the cell line will allow for cell surface expression of the protein.

A cell expressing a protein of the invention is typically obtained by transfecting a cell with a vector of the invention and maintaining the cell under conditions suitable for obtaining expression of the protein.

The invention also includes a cell expressing a protein of the invention which cell is bound to or infected with the virus to which the extracellular domain of a protein of the invention expressed in said cell is capable of binding. A cell expressing the protein of the invention may be infected with a virus by contacting the cell with a virus under conditions suitable for binding of the virus to the protein of the invention. The viral infection of the cell may be detected by any suitable means. For example, following viral exposure the virus bound on the surface of a cell may be removed by acid wash and the cells may be permeabilised and stained with an antibody to the virus to detect any viruses that have been internalised into the cell.

Transgenic Animals

A protein of the invention may be expressed in cells of a transgenic non-human animal. The transgenic non-human animal is typically of a species commonly used in biomedical research and is preferably a laboratory strain. Suitable animals include non-human primates and rodents. It is preferred that an animal of the invention is a rodent, particularly a mouse, rat, guinea pig, ferret, gerbil or hamster. Most preferably an animal of the invention is a mouse.

A non-human transgenic animal of the invention may be generated using any appropriate protocol. A suitable method comprises:

(i) making a suitable cell of the invention;

(ii) allowing the cell to develop into an animal of the invention; and (iii) optionally, breeding the animal true.

An expression vector of the invention may be introduced into a non-human animal embryo by micro-injection. Or alternatively, embryonic stem cells may be used. Whichever approach is taken, transgenic animals are then generated. The founder animals that are obtained can be bred. The pro-nuclear microinjection method is preferred, in which a vector of the invention is injected into the pronucleus of a fertilized ocyte of a non-human animal.

A transgenic animal can be analysed for the presence of a polynucleotide of the invention (transgene) in any suitable fashion. Typically, genetic DNA from an animal is screened using PCR primers in the polynucleotide coding sequence. The results are typically confirmed by blotting the genetic DNA from the positive samples and probing with a radiolabeled polynucleotide of the invention. Expression of a protein of the invention in cells of a transgenic animal can be determined using immunoblotting techniques for example using an anti-F(ab') antibody or an antibody to the extracellular domain of a cell surface receptor which comprises the extracellular domain of a protein of the invention.

A transgenic non-human animal of the invention may be infected with a virus, which virus is capable of binding to the extracellular domain of a protein of the invention which is expressed in a cell of the transgenic animal. A transgenic animal may be infected with a virus by exposure to a viral sample by any suitable method.

A typical viral sample may comprise infectious sera prepared from another infected animal, including a human, an infectious tissue culture preparation such as infected cells or sup ematent from an in vitro culture or an infectious RNA preparation. Typically a viral sample is administered directly to the transgenic animal. For example, the animal may be infected by intravenous injection of the virus. The virus may be administered at any appropriate dosage. A typical dose may be 0.1 ml of viral infection serum, preferably 0.2 to 0.5 ml.

A transgenic animal of the invention may express a protein of the invention in a specific tissue or cell type such that a specific tissue or cell type is infected with the virus. Tissue- or cell-specific expression of a protein of the invention is achieved using an expression vector in which a polypeptide of the invention is operably linked to a tissue-specific promoter. For example, HCV infects human liver cells. It is therefore preferred that a transgenic animal expressing a protein of the invention capable of binding to HCV expresses the protein in a liver-specific manner. Similarly, it is preferred that a protein of the invention capable of binding HBV is expressed in liver cells, that a protein of the invention capable of binding HIV is expressed in T-cells and/or brain cells, that a protein of the invention capable of binding rabies virus is expressed at neuromuscular junctions, that a protein of the invention capable of binding reovirus type 3 is expressed in neurons and that a protein of the invention capable of binding Rotavirus is expressed in gut epithelium.

Screening Methods

Cells and transgenic animals according to the invention may be used in methods in screening and testing potential anti-viral agents. An anti-agent is capable of inhibiting viral entry into a cell, survival of a virus, viral protein synthesis, viral replication or spread of a virus. Thus, an anti-viral agent may be used as a vaccine to prevent viral infection or as a therapeutic agent to treat a viral infection.

A method for identifying an anti-viral agent, typically comprises:

(i) providing a cell expressing a protein of the invention or a non-human human transgenic animal expressing a protein of the invention;

(ii) infecting the cell or animal with a virus;

(iii) contacting the cell or animal with a test agent; and (iv) monitoring viral infection;

thereby determining whether the test agent has anti-viral activity.

A method for identifying an anti-viral agent suitable for preventing a viral infection typically comprises:

(i) providing a cell expressing a protein of the invention or a non-human transgenic animal expressing a protein of the invention;

(ii) contacting the animal or cell with a test agent;

(iii) contacting the cell or animal with a virus capable of binding to said protein; and (iv) monitoring for infection;

thereby determining whether the test agent prevents or limits viral infection.

Where the method utilises a non-human transgenic animal of the invention, the test agent and/or the virus may be administered to the said animal by any suitable method. Examples of suitable methods of administration are included herein.

Cells expressing a protein of the invention may be contacted in vitro with a test agent by any suitable method. The cells may be perfused with the test agent or the agent may be added to the culture medium bathing the cells. The test agent may be introduced into the cells directly. Any suitable technique known in the art may be used to introduce the test agent into the cultured cells. Such well-known techniques include microinjection, electroporation and methods involving the use of transfection agents such as lipofectants, DEAE-dextran and calcium phosphate.

Viral infection may be monitored by any suitable method. For example, death of host cells, viral replication, protein synthesis or the presence of viral protein on the surface of host cells may be monitored. Suitable methods for monitoring viral infection are described in Chesebro and Wehrly (1988), J. Virol. 62,3779-3788 and in Pincus et al (1989), J. Immunol. 142, 3070-3075.

HIV infection may be monitored using commercially available kits. For example, an HIV-I p24 ELISA (Coulter Inc, R&D Systems Inc.) or a RT-RCR kit for HIV long terminal repeat (LTR): NASBA [nucleic acid sequence-based amplification] (Amplicar (Roche Diagnostics)) may be used. Suitable assays are also described in the following documents: Steiger et al. (1991), J. Virol. Methods 34(2): 149-160, Byrne et al. (1998), Nucleic Acids Res. 16(9): 4165, Vandamme et al. (1995), J. Virol. Methods 52(1-2): 121-132 and Bolton et al. (1987), J. Clin. Microbiol. 25(8): 1411-1415.

HCV infection may be monitored using commercially available kits for the quantitative (Chiron bDNA signal amplification method) or qualitative (Cobas amplicor, Roche Diagnostics) RT-PCR for the 5' non coding region. Use of suitable assays are also described in Lunel et al. (1999), Hepatology 29(2): 528-535, Yeh et al. (1997), J. Virol. Methods 65(2): 219-226 and Jacob et al. (1997), Am. J. Clin. Pathol. 107 (3): 362-367.

HBV infection may be monitored by quantitative PCR (Chiron bDNA signal amplification method; Cobras amplicor (Roche Diagnostics); Digene Diagnostics, Inc. (DNA: RNA hybridisation)). Suitable assays are described in Khakoo et al. (1996), J. Med. Virol. 50(2) 112-112-116 and Chen et al. (1995), J. Virol. Methods 53(1):131-137.

Test substances may be used at a concentration of from 1 nM to 1000 µM, preferably from 1 µM to 10 µM, more preferably from 1 µM to 10 µM. A test substance which has anti-viral activity may reduce viral infection by more than 50%, 60%, 70%, 80%, 90% compared to viral infection in a control animal or cell.

Suitable test substances include combinatorial libraries, defined chemical entities and compounds, peptide and peptide mimetics, oligonucleotides and natural product libraries, such as display (e.g. phage display libraries) and antibody products.

Typically, organic molecules will be screened, preferably small organic molecules which have a molecular weight of from 50 to 2500 daltons. Candidate products can be biomolecules including, saccharides, fatty acids, steroids, purines, pyrimidines, derivatives, structural analogs or combinations thereof. Candidate agents are obtained from a wide variety of sources including libraries of synthetic or natural compounds. Known pharmacological agents may be subjected to directed or random chemical modifications, such as acylation, alkylation, esterification, amidification, etc. to produce structural analogs.

Therapeutic Uses

An agent identified by a method of the invention may be used in a method of therapeutic or prophylactic treatment of the human or animal body by therapy. The invention provides a method for treating a patient infected with a virus, the method comprising administering to the patient a therapeutically effective amount of an agent identified by a method of determining anti-viral activity of the agent according to the invention. The patient is generally infected with a virus against which the anti-viral agent has been shown to have anti-viral activity. The patient may be infected with HCV, HIV, HSV-1, HSV-2, Influenza A, Influenza B, RSV, Rhinovirus, Coxsackie virus or HBV. Preferably the patient infected with a viral infection is suffering from symptoms of the viral infection. For example, a patient infected with HCV is preferably suffering from hepatitis C.

The invention provides a method for treating a subject at risk of viral infection, the method comprising administering to the said subject a prophylactically effective amount of an agent identified by a method of the invention. The invention also provides a method for the treatment of a patient infected with a virus but not suffering from symptoms of a disease caused by the virus in order to prevent the patient developing said disease. This method comprises administering an amount of an agent which is effective in preventing onset of disease symptoms to a patient infected with the virus.

It is preferred that therapeutic treatment is administered in the early stages of infection. Complications of viral infection, such as cirrhosis, portal hypertension, hepatocellular carcinoma which are complications of hepatitis C may also be treated using an agent identified by a method of the invention.

An agent for use in a method of treatment of a viral infection by therapy will typically improve the condition of a patient suffering from the infection and/or ameliorate the symptoms of the infection.

An agent for use in a method of prophylatic treatment of a viral infection or disease caused by a viral infection will typically lessen the severity of one or more of the symptoms resulting from infection and/or may prevent the onset of one or more symptom of infection.

An agent identified according to a screening method outlined above may be formulated with standard pharmaceutically acceptable carriers and/or excipients as is routine in the pharmaceutical art, and as fully described in Remington's Pharmaceutical Sciences, Mack Publishing Company, Eastern Pennsylvania $17^{th}$ Ed. 1985, the disclosure of which is included herein of its entirety by way of reference. Compositions and medicaments for use in a method of treating a viral infection may be formulated in dosage form. Medicaments comprising a therapeutic agent identified by a method of the invention may be in a form suitable for administration to a patient, for example in tablet, capsule or liquid form, or may be in a concentrated form suitable for preparation by a pharmacist.

The agents may be administered by external or parental routes such as via oral, buccal, anal, pulmonary, nasal, vaginal, intravenous, intra-arterial, intrahepatic, intramuscular, intraperitoneal, subcutaneous or other appropriate administration routes.

A therapeutically effective amount of an agent is administered to a patient. An amount of an agent sufficient for preventing infection is administered to a subject at risk of viral infection. The dose of a therapeutic agent may be determined according to various parameters, especially according to the substance used; the age, weight and condition of the patient to be treated; the route of administration;

and the required regimen. A physician will be able to determine the required route of administration and dosage for any particular patient. A typical daily dose is from about 0.1 to 50 mg per kg of body weight, according to the activity of the specific agent, the age, weight and conditions of the subject to be treated, the type and severity of the disease and the frequency and route of administration. Preferably, daily dosage levels are from 5 mg to 2 g.

An agent that is capable of preventing viral infection by stimulating the immune system to produce antibodies specific for proteins of the virus is preferably administered in a single dose. One or more further doses may be required for long term protection against hepatitis infection. Further doses may be administered after a period of 1 to 15 years after the initial dose, for example after 1, 2, 3, 4, 5, 8, 10, 12 or 15 years. Regular doses may be administered at regular intervals after the first dose, for example at 3, 5, 8, 10 or 15 yearly intervals.

An agent that is capable of preventing viral infection by stimulating the immune system of a mammal to produce antibodies specific for proteins of the virus is preferably a nucleic acid. Nucleic acid, such as RNA or DNA, and preferably, DNA, is provided in the form of a vector which may be expressed in the cells of the mammal.

Such nucleic acids may be administered to the animal by any available technique. For example, the nucleic acid may be introduced by injection, preferably intradermally, subcutaneously or intramuscularly. Alternatively, the nucleic acid may be delivered directly across the skin using a nucleic acid delivery device such as particle-mediated gene delivery. The nucleic acid may be administered topically to the skin, or to the mucosal surfaces for example by intranasal, oral, intravaginal, intrarectal administration.

Uptake of nucleic acid constructs may be enhanced by several known transfection techniques, for example those including the use of transfection agents. Examples of these agents includes cationic agents, for example, calcium phosphate and DEAE-Dextran and lipofectants, for example, lipofectam and transfectam. The dosage of the nucleic acid to be administered can be altered. Typically the nucleic acid is administered in the range of 1 pg to 1 mg, preferably to 1 pg to 10 μg nucleic acid for particle mediated gene delivery and 10 μg to 1 mg for other routes.

The following Examples illustrate the invention.

Materials and Methods

Cell Lines

The human embryonic kidney cell line, 293, and its derivative, 293T, bearing the large T antigen from SV40 were purchased from American Type Cell Collection (Manassas, Va., USA). Huh7 cells were obtained from Japan Health Sciences Foundation (Chou-ku, Osaka, Japan). HepG2 and U937 cells were also purchased from American Type Cell Collection. All cells were cultured at 37° C. in 5% $CO_2$ in EMEM, DME or MEM containing 2 mM L-glutamine, 1.5 g/L sodium bicarbonate, 0.1 mM non-essential amino acids, 1 mM sodium pyruvate, and 10% fetal bovine serum.

EXAMPLE 1

Generation of Wild-type CD81, Chimeric CD81 and Truncated HCV E2(aa384-661) Expression Constructs cDNA of the human full length wild-type CD81 (CD81WT) was obtained by RT-PCR (primers C1 and C2, Table 1) from total cellular RNA of U937 cells and cloned into BamHI/EcOR1 sites of pcDNA3.1+(Invitrogen, Carlsbad, Calif., USA). For CD81-transferrin receptor chimera (CD81-ΔTFR), the N-terminal cytoplasmic domain was obtained by PCR from the full-length transferrin receptor (primers C3 and C4, Table 1) and ligated to the N-terminal of pcDNA3-CD81WT (Hind III, BamHI). For CD81-LDLR chimera (CD81-ΔLDLR); the C-terminal cytoplasmic domain of LDLR was obtained by RT-PCR using total cellular RNA of HepG2 cells (C5 and C6, Table 1). PCR product was then ligated to the C-terminal of a pcDNA3-CD81WT clone whose stop codon has been removed by PCR method (EcORI, NotI). A schematic representation of the different constructs is shown in FIG. 1A.

The sequence of HCV E2 cDNA from aa 384-661 was PCR amplified from the HCV genome of HCV-S1 of genotype 1b (Lim et al. Virus Genes 23, 89-95, 2001) and cloned into the BamHI and EcOR5 sites of pSecTagC from Invitrogen. Primers used are C7 and C8 (Table 1).

TABLE 1

Primers used for cloning of constructs and detection of viral transcripts.

(SEQ ID NOS 1-16, respectively, in order of appearance)

| | |
|---|---|
| C1 | 5'-AAAGCTAGCGGATCCGCCACCATGGGAGTGGAGGGCTGCAC CAAGTGCATCAAGT-3' |
| C2 | 5'-AAAGAATTCGCGGCCGCTCAGTACACGGAGCTGTTCCGGAT GCCACAGCACAGCACCATGCTCAG-3' |
| C3 | 5'-CCCAAGCTTACCATGGCGATGATGGATCAAGCTAGATCA GCA-3' |
| C4 | 5'-CGCGGATCCCCTTTTTGGTTTTGTGACATTGGC-3' |
| C5 | 5'-CCGGAATTCAAGAACTGGCGGCTTAAGAACATC-3' |
| C6 | 5'-ATAAGAATGCGGCCGCTCACGCCACGT CATCCTCCAG-3' |
| C7 | 5'-GGGGGATCCACCACACCCAAGTGATGGGGG-3' |
| C8 | 5'-GGGGATATCTCTCTGATCTATCCCTGTCCTC-3' |
| P1 | 5'-ACTCATTCCCATTCTGCAGCTTCC-3' (nt 10-28) |
| P2 | 5'-CTGTGAGGAACTACTGTCT-3' (nt 36-55) |
| P3 | 5'-CGGTGTACTCACCGGTTCC-3' (nt 161-143) |
| P4 | 5'-ACTCGCAAGCACCCTATCA-3' (nt 303-285) |
| P5 | 5'-TCGCGACCCAACACTACTC-3' (nt 274-256) |
| P1TAG | 5'-TCATGGTGGCGAATAAACTCATTCCCATTCTGCAGCTT CC-3' |
| TAG | 5'-TCATGGTGGCGAATAA-3' |
| HCV probe: | 5'-GCAGAAAGCGTCTAGCCATGGCGTTAGTAT-3' (nt 68-97) |

EXAMPLE 2

High Level of CD81 Expressions on the Surface of Stable Huh7 Clones

Transient transfection experiments were performed using Effectene™ transfection reagent from QIAGEN (Valencia, Calif., USA), according to the manufacturer's protocol. Stable CD81 clones expressing wild-type CD81 (CD81WT), CD81 fused at the N-terminal with 61 amino-acids of the cytoplasmic domain of transferrin receptor (CD81-ΔTFR), and CD81 fused at the C-terminal with 50 amino-acids of the cytoplasmic domain of LDL receptor (CD81-ΔLDLR) were generated by electroporation of 20 μg DNA into about $5 \times 10^6$ Huh7 cells at 0.25 kvolts using a BIORAD (Hercules, Calif., USA) gene pulser machine. Cells were selected by growing in 1 mg/ml of geneticin (GibcoBRL, Gaithesburg, Md., USA) and single colonies were isolated and analyzed for surface expression by FACScan analysis using antibodies specific for CD81, LDL and transferrin receptors. Stable Huh7 clones were harvested, washed in PBS and resuspended at $1 \times 10^6$ cells/ml. 0.5 ml of cells were incubated with a mouse anti-human CD81 antibody or an isotype-matched control from BD PharMingen (San Diego, Calif., USA) for 30 min at 4° C., washed and re-incubated with a goat anti-mouse antibody conjugated with phycoerythrin (Sigma, St. Louis, USA). Cells were washed and analyzed on a Becton Dickinson flow cytometer (San Jose, Calif., USA). Live cells were gated and a total of 10 000 events were collected per analysis. For stable Huh7 cells expressing wild-type CD81, high-expressing clones were isolated by FACS-sorting. Untransfected parental Huh7 expressed low levels of CD81 receptors whereas the 3 stable clones (CD81WT, CD81-ΔTFR and CD81-ΔLDLR) all showed high levels of expression (FIG. 1B). The expression levels of endogenous transferrin and LDL receptors in the three stable clones did not vary significantly from the levels of these receptors in untransfected Huh7 cells. 293T cells expressing endogenous CD81, LDL and transferrin receptors were used as positive controls. FACScan analysis for transferrin and LDL receptors was performed using antibodies from BD PharMingen and Oncogene Research Products (Cambridge, Mass., USA) respectively.

EXAMPLE 3

Chimeric Receptors, CD81-ΔTFR and CD81-ΔLDLR, Internalize More Efficiently than CD81

$50 \times 10^5$ cells were plated on 6-well plates and allowed to settle overnight. 0.5 ml of 10 μg/ml of CD81 monoclonal antibody (Santa Cruz Biotechnology, Santa Cruz, Calif., USA) was overlaid onto the cells for 1 h at 37° C. After cooling on ice for 10 min, any unbound antibody was removed with 3 washes of cold PBS and surface-bound antibody was stripped by incubating the cells with cold 0.2 M acetic acid/0.5 M NaCl for 5 min, followed by PBS washes. Cells were harvested and lysed in Laemmli's SDS buffer and subjected to western analysis. Briefly, total protein was separated on a 10% SDS-polyacrylamide gel and transferred to a nitrocellulose membrane. Then, the membrane was blocked with 5% non-fat dry milk and incubated with goat anti-mouse horse-radish peroxidase (HRP) conjugated antibody (Pierce, Rockford, Ill., USA) for 1 h, followed by detection using an enhanced chemiluminescence method (Pierce).

Figure 2:
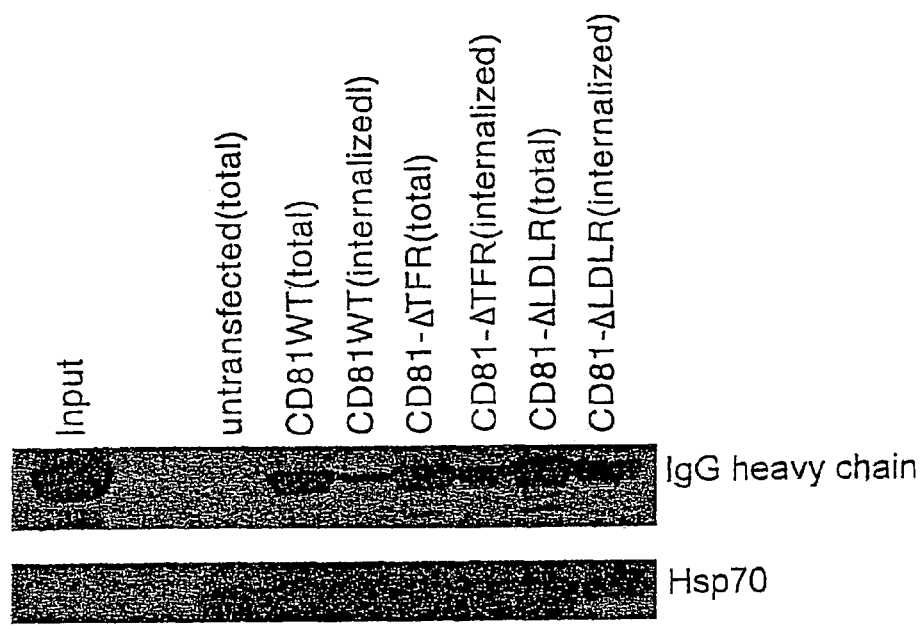
FIG. 2 shows the results of western analysis of the internalization of anti-CD81 antibodies via wild-type and chimeric CD81. Total IgG in the cell lysate represents both surface-bound and internalized antibody after living cells were allowed to endocytose antibody for 1 h at 37° C. Only internalized IgG was left in the cell lysate after an acid wash was used to remove all surface-bound antibody. Expression of intracellular heat shock 70 protein, Hsp70, was used for normalization.

The heavy chain of the antibody (both surface-bound and internalized) was observed in CD81WT, CD81-ΔTFR and CD81-ΔLDLR cells (after washes with PBS to remove any unbound antibody from the surface) FIG. 2). As expected, little binding of anti-CD81 antibody to untransfected Huh7 cells was observed. When an additional 5 minute acid wash was used to remove the surface bound CD81 antibody, ~30% of anti-CD81 antibody (total amount of surface-bound and internalized antibodies was normalized to 100%) remained in the intracellular fractions of Huh7-CD81WT cells (FIG. 2). Exposure to antibody for more than 1 h also did not result in a significant increase in intracellular accumulation of anti-CD81 antibody in Huh7-CD81WT cells.

In Huh7-CD81-ΔTFR and Huh7-CD81-ΔLDLR, a higher percentage (70%) of anti-CD81 antibody was internalized, showing that the fusion of cytoplasmic domains from the two recycling receptors, transferring receptor and LDL receptor, to CD81 have greatly increased the internalization efficiency of the receptor (FIG. 2). The fusion of these cytoplasmic domains at the N-terminal (CD81-ΔTFR) or C-terminal (CD81-ΔLDLR) of CD81 appeared to increase the internalization of CD81 to the same extent.

To determine the intracellular localization of wild-type and chimeric CD81 receptors, cells were fixed with 3.7% formaldehyde for 10 min at room temperature, following by 10 min permeabilization with 0.2% Triton-X 100, 3.0 min blocking with PBS containing 1% purified BSA (Sigma), 2 h incubation with an anti-CD81 monoclonal antibody (Santa Cruz) and finally 1 h incubation with a FITC-conjugated goat anti-mouse antibody (Santa Cruz). Slides were mounted and pictures taken on a MRC1024 laser confocal microscope (BIORAD).

In all three stable cell lines, punctuate staining around the nucleus was observed, indicating intracellular localization of wild-type and chimeric CD81 receptors to the endosome structures.

In order to determine the path of the receptors after internalization, living cells were overlaid with anti-CD81 antibody for 1 h, followed by acid-stripping of surface-bound antibody. The cells were then permeabilized as before and probed with an FITC-conjugated anti-mouse antibody for the presence of internalized anti-CD81 antibody. For Huh7-CD81-ΔTFR and —CD81-ΔLDLR cells, strong intracellular staining were observed, showing that anti-CD81 antibody was internalized and transported to the endosomes, which is the compartment where uncoupling between ligand and receptors normally occurs. Consistent with the lower internalization efficiency of wild-type CD81, Huh7-CD81WT cells showed little intracellular staining in this experiment.

It should be noted that the measurement of intracellular (i.e. non-acid removable) CD81 antibody as a probe for the internalization of CD81 receptor is only comparative and may be an underestimation as some of the internalized antibody may be degraded. For example, because rapid intracellular degradation of the antibodies is occurring after internalization.

EXAMPLE 4

Chimeric Receptors, CD81-ΔTFR and CD81-ΔLDLR, Undergo Greater Cell Surface Re-cycling Compared to CD81

The rate of down-modulation and re-expression of both wild-type and chimeric CD81 on the cell surface of the various stable clones was determined over a period of 8 h by FACScan analyses. Cells were incubated with 10 μg/ml of anti-CD81 monoclonal antibody for 1 to 8 h, followed by PBS washes, and then FACScan analysis carried out as described above to determine amount of receptors on cell surface. Mean fluorescence of cells was determined for each time point.

Figure 3:
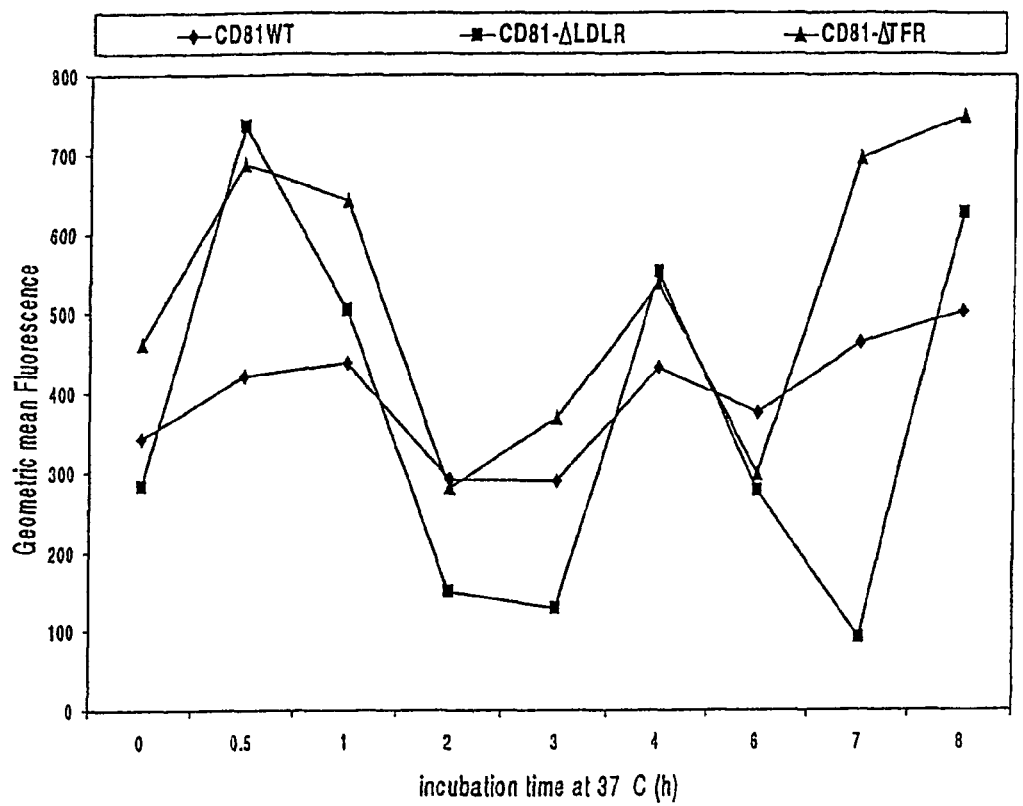
FIG. 3 shows the rate of down modulation and re-expression of both wild-type and chimeric CD81 receptors on the cell surface of Huh7 stable clones as determined by FACScan analysis. Surface expression of CD81 receptors was determined after the cells were incubated with an anti-CD81 antibody at 37° C. for different times, washed extensively and incubated with anti-CD81 antibody and phycoerythrin-conjugated goat anti-mouse IgG. Mean fluorescence was then computed for each time-point.

In general both wild-type and the chimeric CD81 molecules underwent a 4 h cycling profile (FIG. 3). CD81WT and CD81-ΔTFR both showed a similar profile, with maximum internalization and re-expression both occurring within a period of 2 h (FIG. 3). Down-modulation of CD81-ΔLDLR molecules occurred maximally after a 3 h of exposure to antibody, with re-expression taking place within 1 h later (FIG. 3). Nevertheless, both chimeric CD81 molecules were internalized to a greater degree compared to CD81WT, up to 60% and 44% of CD81-ΔTFR and 79% and 50% of CD81-ΔLDLR molecules were internalized, after 2 and 6 h respectively, of incubation at 37° C., compared to only 33% and 13% of CD81WT (Table 2). In the case of CD81-ΔLDLR molecules, these continued to be down-modulated, resulting in up to 82% and 83% internalization at the end of 3 and 6 h respectively of incubation (Table 2). Moreover, re-expression of chimeric CD81 molecules on the surface was significantly more pronounced than wild-type CD81. There was an increase in 90% and 150% of surface CD81-ΔTFR and in 325% and 566% of surface CD81-ΔLDLR molecules within the periods of 3-4 h and 7-8 h respectively, of incubation with antibody, compared to only 47% and 33% re-expression in CD81WT at the same time periods (Table 2).

TABLE 2

Geometric means fluorescence

| | Incubation at 37° (h) | CD81-WT | CD81-ΔLDLR | CD81-ΔTFR |
|---|---|---|---|---|
| 1 | 0 (unstained) | 4.42 | 2.12 | 3.19 |
| 2 | 0 | 345.51 | 284.37 | 465 |
| 3 | 0.5 | 425.25 | 736.66 | 689.68 |
| 4 | 1 | 441.27 | 505.68 | 645.3 |
| 5 | 2 | 295.69 | 152.66 | 284.11 |
| 6 | 3 | 293.43 | 130.16 | 370.81 |
| 7 | 4 | 436.11 | 553.42 | 540.88 |
| 8 | 6 | 379.9 | 279.62 | 300.58 |
| 9 | 7 | 468.3 | 94.15 | 697.91 |
| 10 | 8 | 506.24 | 627.11 | 750.86 |

EXAMPLE 5

Binding of Soluble form of HCV E2 Protein to Cell Surface of Huh7 Stable Clones

A secreted and soluble form of E2, which lacks the C-terminal hydrophobic transmembrane anchor was expressed in 293T cells by transient transfection with pSec-TagC-E2 using Superfect reagent (Qiagen). 3 days post-transfection, culture medium was cleared and secreted E2 proteins were captured on NTA-nickel sepharose beads (Qiagen). The beads were washed with PBS and E2 was eluted with 1 M imidazole solution, followed by centrifugal filtration (Millipore, Bedford, Mass., USA) to remove the imidazole. The pSecTag vector (Invitrogen) contains a secretion signal from the V-J2-C region of the mouse IgG kappa-chain.

Virtually all the expressed E2 protein was secreted into the growth medium and could be purified with NTA-nickel sepharose beads as it is fused with a C-terminal polyhistidine tag. In the absence of reducing agent, the purified protein separated on SDS-PAGE to give two bands: a high molecular weight species >111 kDa (~80%) and a ~70 kDa species (~20%) (FIG. 4A). The addition of reducing agent resulted in the dissociation of the higher molecular weight species to give only a 70 kDa band on SDS-PAGE (FIG. 4A). This suggests that the majority of the E2 purified were in the form of disulphide-linked aggregates (>111 kDa), which could be dissociated by the addition of reducing agent. The monomeric E2 exhibited a lower mobility (70 kDa) than the molecular weight predicted from the peptide sequence (~36 kDa), indicating that the protein was heavily glycoslyated.

A mixed population of E2 proteins in PBS with 1% BSA was overlaid onto monolayers of cells for four hours to assess E2 binding to cell surface receptors. E2 in PBS with 1% BSA was overlay onto cells for 4 h. Cells were washed 3 times with cold PBS, lysed in Laemmli's SDS buffer and bound E2 were determined by western analysis using an anti-c-myc monoclonal antibody (Santa Cruz) to detect the C-terminal myc-tag fused to the E2 protein.

FIG. 4B shows that E2 bound to Huh7-CD81WT, Huh7-CD81-ΔTFR and Huh7-CD81-ΔLDLR, but not to untransfected Huh7 cells. These results suggest that E2 can bind to the extracellular domain(s) of CD81, which is present in all these stable cell-lines. However, the association rate appeared to be quite slow as bound E2 was only detected after 4 hrs. This is likely to be due to the low concentration of monomeric E2 expressed in this system as it has been shown previously that only monomeric E2, and not aggregated E2 oligomers, is capable of binding CD81.

EXAMPLE 6

Chimeric Receptors, CD81-ΔTFR and CD81-ΔLDLR Mediate Efficient Entry of HCV Virions into Huh7 Cells The ability of the stable CD81-Huh7 clones to support HCV entry was tested by culturing Huh7 cells stably expressing an inducible full length HCV genome (clone SH9; Lim et al., 2001) for 5 days, with or without tetracycline (tet) (Sigma), after which the culture media was removed, spun at 2500 rpm for 5 min, aliquoted and frozen at −80° C. 800 μl of culture media was layered onto 2.5×10$^5$ Huh7 cells and stable CD8'-Huh7 clones in 60 mm petri dishes. The cells were added with 1.2 ml complete media and incubated for 6-8 h at 37° C., after which they were washed 6 times with PBS, added with 4 ml of fresh media and re-incubated for 5 days at 37° C. At the end of the period, the cells were washed 3× with PBS and total cellular RNA was extracted with the Trizol reagent from Gibco BRL, according to the manufacturer's protocol, followed by treatment with 5U of DNaseI (Promega, Madison, Wis., USA) at 37° C. for 30 min.

The presence of viral particles in the culture media from these cells was determined by RT-PCR after an antibody capture method using beads bound with anti-E2 monoclonal antibodies. 5 μg of anti-E2 (H52, kindly provided by Dubuisson, J, Flint et al., J. Virol. 73, 6235-6244, 1999) were bound over-night onto. 10 μl packed volume) of protein A/G beads (Oncogene Research Products) at 4° C. Beads were washed twice in PBS and incubated with culture media for 2 h at 4° C. After incubation, the beads were washed extensively in PBS before RT-PCR was carried out. For pre-clearing of the culture medium, a similar protocol was performed except, after incubation of culture media with antibody, bound beads (anti-E2 or anti-c-myc for control), the beads were spun down at 14 000 rpm for 5 min at 4° C. and the culture media removed and layered onto cells.

Primers for RT-PCR to detect plus- and minus-strand RNA are listed in Table 1. A 5 μl volume of the RNA was reverse transcribed at 42° C. for 1 h using the specific antisense primer and 200 U of Superscript II™ (Gibco BRL. Life technologies), followed by heating at 100° C. for 1 h, and treatment with 2.5 μg RNase A for 30 min at 37° C. PCR was carried out with Platiniurn Taq polymerase (Gibco BRL. Life technologies). The first PCR reaction was performed with 5 μl of template in a total volume of 50 μl followed by second round of PCR with 1 μl of the first PCR reaction. For the detection of plus-strand RNA, PCR was performed with P1 and P4, followed by P2 and P3 or P5. For the detection of minus-strand RNA, RT was carried out using the tagged primer, P1-TAG (Lanford et al., Virology 202, 606-614, 1994). The first round of PCR was carried out with TAG and P4 and the second round with TAG and P3 or P5. PCR conditions are as follows: 95° C. for 3 min, followed by 30 cycles of 95° C. for 20 sec, 60° C. (plus strand) or 49° C. (minus strand) for 20 sec, 72° C. for 30 sec and a final extension 72° C. for 8 min. Amplified products were visualized by ethidium bromide staining in a 3% agarose gel.

To determine the specificity of the products obtained by PCR amplification, 25 μl of the PCR products were Southern blotted onto Hybond N+ membrane (USB-Amersham). Hybridisation was carried out with a $^{32}$P-end-labelled oligonucleotide corresponding to nt 68 to 97 of the 5'NCR (HCV probe) in 5 ng labelled DNA per ml hybridisation buffer (6×SSC, 1× Denhardt's solution, 0.05% Na pyrophosphate, and 100 μg/ml sheared salmon sperm DNA). The filters were incubated at 65° C. for 14-16 h after which they were washed twice at 65° C. in 1×SSC-0.1% SDS and 0.5×SSC-0.1% SDS. The filters were then air-dried and exposed to autoradiography films at –70° C. for 4-12 h. Quantification of all authoradiographs was carried out on a BIORAD densitometer.

Figure 5:
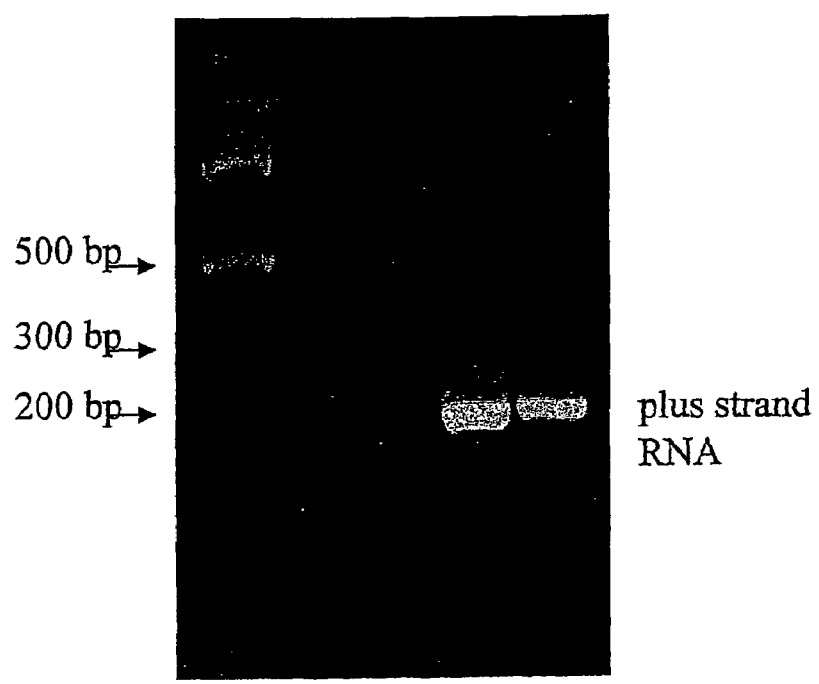
FIG. 5 shows the results of RT-PCR which was performed to assay for the presence of viral transcripts in the culture media from Huh7 cells stably expressing an inducible full length HCV genome. Positive RT-PCR products were observed in culture media from cells that had been induced with tetracycline for 5 days (after antibody capture with anti-E2 antibody) and these products were still observed after treatment with DNaseI and RNaseA. No product was observed if the cells were not induced with tetracycline.

Positive RT-PCR products were observed in culture media of tet-treated cells, but not in untreated cells (FIG. 5, lanes 1 and 3). In addition, these products were still observed after treating the beads with DNaseI and RNaseA after incubation with culture media from tet-treated cells (FIG. 5, lane 4), indicating that the bands were not a result of contamination from DNA or RNA in the media.

Figure 6:
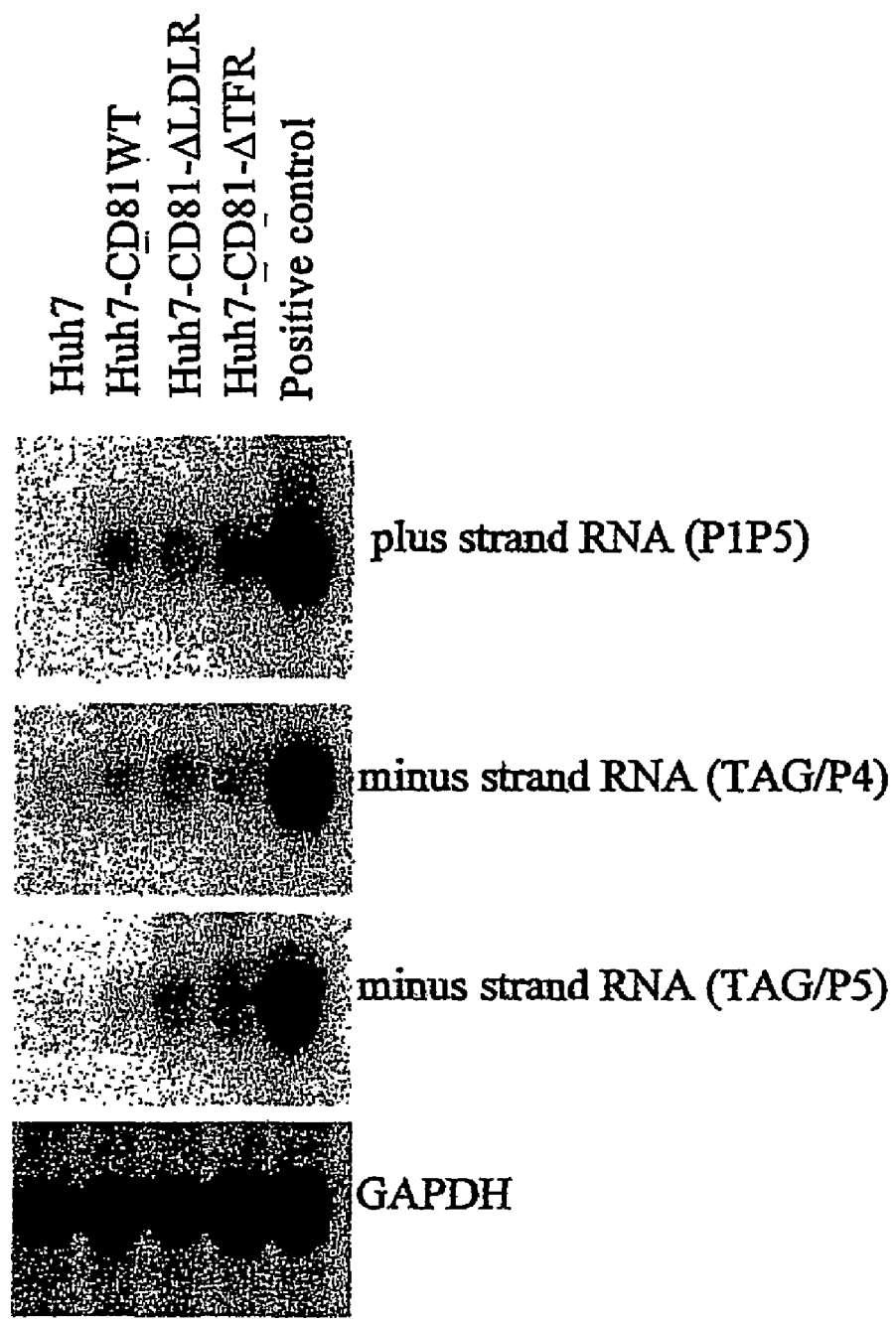
FIG. 6 shows the results of the RT-PCR which was performed to assay for the presence of viral transcripts in Huh7 stables clones after they were exposed to infectious media. Huh7-CD81WT showed a low amount of viral transcript while none was detected in parental Huh7 cells. Huh7-CD81-ΔLDLR and Huh7-CD81-ΔTFR expressing cells exhibited increased levels of both plus and minus strand viral RNA compared to Huh7-CD81WT, indicating an increase in viral uptake and replication in these cells. Cellular GAPDH was used for normalization and positive control was done using RNA from cells transfected with the HCV full-length genome.

Culture media was layered onto either fresh parental or CD81-expressing Huh7 cells for a period of 6-8 h, after which period the cells were washed extensively and reincubated with fresh media for 5 days. Total RNA was subsequently extracted and RT-PCR performed to assay for the presence of viral transcripts. Little plus strand RNA was found in parental Huh7 cells 5 days after exposure to infectious media (FIG. 6, lane 1). On the other hand, a low amount of viral transcript was found in Huh7 cells overexpressing CD81WT (FIG. 6, lane 2). Both Huh7-CD81-ΔLDLR and Huh7-CD81-ΔTFR exhibited increased levels in viral transcripts (FIG. 6, lanes 3 and 4) and the values were at least 2.6 and 6.9 fold higher than that observed with Huh7-CD81WT, after normalization with cellular GAPDH (FIG. 6). No viral products were obtained from cells infected with media derived from control un-induced cells.

To ensure that virus replication had indeed taken place in the infected cells the presence of minus strand was determined using the method described by Lanford et al. (1994) that utilizes a tagged reverse primer. Using a combination of the tagged reverse primer and two different forward primers, we found a similar trend in the expression of minus transcript in the four cell lines (FIG. 6). No product was obtained with parental Huh7 cells, whilst both Huh7-CD81-ΔLDLR and Huh7-CD81-ΔTFR cells contained more minus transcripts compared to Huh7-CD81WT cells (FIG. 6). They were respectively 2.7-5.8 and 2.8-10.7 folds more than the latter after normalization with cellular GAPDH (FIG. 6).

To confirm the authenticity of the results from the above infection studies, blocking experiments were carried out using anti-E2 and —CD81 antibodies. First culture media from tet-treated HCV-Huh7 cells was pre-incubated with beads coated with anti-E2 or control anti-c-myc antibodies for 2 h, after which they were layered onto fresh Huh7-CD81WT or —CD81-ΔTFR cells. Thereafter the cells were incubated further for 5 days and analyzed as before for the presence of viral transcripts. Pre-incubation of media with anti-c-myc beads failed to block infection of both Huh7-CD81WT and —CD81-ΔTFR cells as both plus and minus strand transcripts were seen after RT-PCR (FIGS. 7A and B, lane 3). Pre-incubation with anti-E2 beads completely abolished viral infection of these cells as no products were obtained (FIGS. 7A and B, lane 4).

In another blocking experiment, Huh7-CD81WT and —CD81-ΔTFR cells were pre-incubated with 2.5 mg/ml anti-human or mouse CD81 antibodies for 30 min before a 6 to 8 hour incubation with infectious media. As was expected, control anti-mouse CD81 antibodies failed to prevent infection as viral RT-PCR products were observed in both Huh7-CD81WT and —CD81-ΔTFR cells (FIGS. 7A and B, lane 5). Anti-human CD81 antibodies prevented infection in Huh7-CD81WT but not in Huh7-CD81-ΔTFR cells (compare FIGS. 7A and B, lane 6). The reason for this difference is unknown, but maybe related to the more pronounced recycling of CD81-ΔTFR compared to CD81-WT (see also FIG. 3)

EXAMPLE 7

Isolation of Anti-gp120 Antibody Heavy (IgH) and Light (IgL) Chains cDNAs from Hydridoma 902 cDNAs that encode for the immunoglobulin heavy (IgH) and light (IgL) chains of the anti-gp120 hydridoma 902 were obtained by RT-PCR methods. The hybridoma 902 (catalog number 521) that produces an anti-HIV-1$_{LAV}$/HTLV-III$_B$ gp120 IgG1 monoclonal antibody was obtained from the NIH AIDS Research & Reference Reagent Program (Chesebro & Wehrly, J. Virol. 62, 3799-3788,1988; Pincus et al., J. Immunol. 142, 3070-3075, 1989). Total RNA was extracted from the hybridoma using a RNeasy kit (Qiagen, Valencia, Calif., USA) and transcripted into cDNA using SuperscriptII RNase reverse transcriptase (GibcoBRL, Gaithesburg, Md., USA). PCR reaction was then carried out using the Expand long template PCR system from Roche Molecular Biochemicals (Indianapolis, Ind., USA) and the following primers (SEQ ID NOS 17-21, respectively, in order of appearance):

```
IgL:
Forward: 5' ACCATGAAGTTTCCTTCTCAACTTCTGCTCTTCC 3'

Reverse: 5' GCGCCGTCTAGAATTAACACTCATTCCTGTTGAA 3'

IgH:
Forward: 5' GGGAATTCATGRAATGSASCTGGGTYWTYCTCTT 3'
and
         5' ACTAGTCGACATGGACTCCAGGCTCAATTTAGTTTT
            CCT 3'
```

-continued (R = A or G; Y = C or T; S = C or G; W = A or T)

Reverse: 5' TTATTTACCAGGAGAGTGGGAGAGGCTCTT 3'

PCR products were cloned into pCRII-TOPO vector using the TOPO TA cloning kit (Invitrogen, Carlsbad, Calif., USA) and DNA sequencing of the plasmids was carried out in the core facility at the Institute of Molecular and Cell Biology. 200 ng of the double-stranded templates and 10 ng of the primer were used for the dideoxy method with the Taq DyeDeoxy terminator cycle sequencing kit and the automated DNA sequencer 373 from PE Applied Biosystems (Foster City, Calif., USA).

Secreted antibodies from the hybridoma were captured onto protein A/G beads (Oncogene Research Products, Cambridge, Mass., USA) and then the beads extensively washed with PBS, before the bound proteins were eluted with Laenunli's SDS buffer by heating at 100° C. for 5 minutes and separated on a 15% SDS-polyacrylamide gel. The two major bands at ~55 kDa and ~20 kDa were excised from the gel and processed for Edman sequencing on a Perkin Elmer machine according to manufacturer's protocols.

N-terminal sequencing of the mature heavy and light chain of the antibody secreted by the hybridoma 902 gave peptide sequences of EVQLQQSGAE (residues 18-27 of SEQ ID NO: 36) and DIQMTQSSSY (residues 21-30 of SEQ ID NO: 36) respectively. These sequences of the mature antibody matched to amino acid number 18 and 21 onwards respectively of the proteins encoded by the cDNAs, thus confirming the correct immunoglobulin genes have been isolated (FIG. 8).

EXAMPLE 8

Cloning of IgL and IgH into Expression Vectors and Construction of Chimeric Proteins IgL was cloned into Kpn I and Not I sites of pXJ41neo and IgH was cloned into Kpn I and Hind III sites of pCep4 vector (Invitrogen).

Chimeric heavy chain IgH-ΔCI-MPR was constructed by fusing the transmembrane domain and the cytoplasmic tail of CI-MPR (aa 2305-2492) to the C-terminal of the full-length IgH clone. Similarly, IgH-ΔLDLR was constructed by the addition of the transmembrane region and cytoplasmic tail of LDLR (aa 790 to 860). C-terminal 188 aa of the human cation-independent mannose 6-phospate receptor (CI-MPR) and 71 aa of the human low density lipoprotein receptor (LDLR) were obtained by RT-PCR using total cellular RNA from HepG2 cells as described above. The primers used were (SEQ ID NOS 22-25, respectively, in order of appearance):

```
CI-MPRfor:  5' CCCAAGCTTGCAGTCGGCGCGGTGCTCAGC 3'
CI-MPRrev:  5' ATAAGAATGCGGCCGCTCAGATGTGTAAGAGGTCCT
               CGTC 3'
LDLRfor:    5' CCCAAGCTTCTGTCCATTGTCCTCCCCATC 3'
LDLRrev:    5' ATAAGAATGCGGCCGCTCACGCCACGTCATCCTC
               CAG 3'
```

The PCR products were then ligated into the 3' end of pCep4-IgH using the Hind III and Not I sites, to give chimeric heavy chains, IgH-ΔCI-MPR and IgH-ΔLDLR respectively.

EXAMPLE 9

Chimeric IgH Associates with IgL and Chimeric Recombinant Antibody Expresses on Cell Surface Transient transfection experiments were performed using Effectene™ transfection reagent from QIAGEN (Valencia, Calif., USA), according to the manufacturer protocol. To generate stable clones that constitutively express the IgL chain, 20 μg of DNA were mixed with about 5×10$^6$ 293 cells and electroporated at 0.25 kvolts using a BIORAD (Hercules, Calif., USA) gene pulser machine. Cells were selected by growing in 0.4 mg/ml of geneticin (GibcoBRL) and single colonies were isolated and total protein analyzed by western analysis. A single clone that expressed high level of IgL was then re-transfected in the same manner with various IgH DNA and cells were selected by growing in 0.2 mg/ml hygromycin B (Roche). Single colonies were isolated and total protein analyzed by western analysis.

Transfected cells were lysed in HBS buffer (10 mM Hepes, 150 mM NaCl, 1% NP40) and total protein concentration determined by Cosmassie Plus reagent from Pierce (Rockford, Ill., USA). 30 ug of total were separated on a 15% SDS-polyacrylamide gel and transferred to nitrocellulose membrane. Then, the membrane was blocked with 5% non-fat dry milk. For detection of IgL protein, the blot was incubated overnight with a horse-radish peroxidase (HRP) conjugated anti-light chain antibody from BD Pharmingen (San Diego, Calif., USA), followed by detection using an enhanced chemiluminescence method (Pierce). For the heavy chain, the blot was incubated with an HRP-conjugated goat anti-mouse (Pierce) antibody before detection.

Transient expression of each chimeric heavy chain respectively together with the full-length light chain (IgL) showed that most of the heavy and light chains are retained in the cell. In contrast, transfection of the original IgH together with IgL resulted in secretion of the recombinant antibody into cell culture medium (FIG. 9A). In addition, there is proper association between the different heavy chains and light chain in solution (either cell culture medium for IgH or cell lysate for IgH-ΔCI-MPR and IgH-ΔLDLR) as capturing the heavy chains with protein A/G beads (which binds to constant region of IgH) also pulled down IgL proteins (FIG. 9A).

Cell surface expression was analysed by FACScan analysis: Transiently transfected 293T cells were harvested, washed in PBS and resuspended at 1×10$^6$ cells/ml. 0.5 ml of cells were incubated with a goat anti-F(ab')$_2$ antibody (9 ug/ml) conjugated with FITC (Pierce) for 30 min at 4° C., washed and analyzed on a Becton Dickinson flow cytometer (San Jose, Calif., USA).

FACScan analysis showed that IgL complexed with IgH-ΔCI-MPR or IgH-ΔLDLR were expressed on the cell surface so that they can bind an anti-F(ab')$_2$ antibody (FITC conjugated) (FIG. 9B). In contrast, cells transfected with the original IgH and IgL were not able to bind the anti-F(ab')$_2$ antibody.

EXAMPLE 10

Cell Surface-displayed Chimeric Antibodies Undergo Internalization

Stable clones, 293-IgH-AM6PR and 293-IgH-ΔLDLR, which expresses high levels of heavy and light chains, were obtained from transfection of 293 cells (FIG. 9C). To determine if these clones can bind and internalize an anti-F(ab')$_2$ antibody, live cells were overlaid with the anti-F (ab')$_2$ antibody to allow endocytosis to occur, followed by PBS washes and cell fixation and confocal microscopy as described below.

30,000 live cells were plated onto poly-D-lysine (Sigma, St Louis; USA) treated 4-well Permanox slide chambers (Nalge Nunc International Corp., IL, USA) and allowed to settle overnight. Then 0.2 ml of 7.5 µg/ml of goat anti-mouse F(ab')$_2$-FITC antibody (Pierce) was overlaid onto the cells for 1 h at 37° C. The plate was then cooled on ice for 5 min before any unbound antibody was removed with 3 washes of cold PBS. For stripping of surface-bound antibody, the cells were further incubated with cold 0.2 M acetic acid/0.5 M NaCl (Haigler et al., J. Biol. Chem. 255, 1239, 1980) for 5 min, followed by PBS washes. Cells were fixed with 3.7% formaldehyde for 10 min at room temperature following by PBS washes. Slides were mounted and pictures taken on a MRC1024 laser confocal microscope (BIORAD).

A large amount of total (surface and intracellular) anti-F (ab')$_2$ antibodies was observed in 293-IgH-ΔCI-M6PR and 293-IgH-ΔLDLR cells but not in the parental 293 cells. When an additional acid wash was included to remove surface bound anti-F(ab')$_2$ antibody before cell fixation, internalized anti-F(ab')$_2$ antibodies were observed in 293-IgH-ΔCI-MPR and 293-IgH-ΔLDLR cells and were localized in intracellular spot-like structures. The data showed that the stable clones are expressing properly assembled chimeric antibodies on cell surface and these chimeric antibodies can be rapidly internalized.

EXAMPLE 11

Antibody Secreted by Hybridoma and Recombinant Antibody Can Bind HIV-1 MC99IIIBΔTat-Rev Virus in Vitro The attenuated HIV-1 MC99IIIBΔTat-Rev virus, which can only propagated in CEM-TART cells that constitutively express tat and rev, provided a safe source of high titre HIV-1 virus. The HIV-1 MC99IIIBΔTat-Rev virus (catalog number 1943) and CEM-TART cells (catalog number 1944) were obtained from the NIH AIDS Research & Reference Reagent Program. Viruses were propagated as previously described and stored at −70° C.

For in vitro binding experiments to confirm that antibodies secreted by hybridoma 902 can recognise the gp120 envelope protein on HIV-1 MC99IIIBΔTat-Rev virus, secreted antibodies from hybridoma 902 were captured onto protein A/G (which binds to IgH constant region), followed by PBS+0.2% NP40 washes and then overnight incubation with HIV-1MC99IIIBΔTat-Rev virus diluted 10 times with the same buffer. The beads were washed and any bound virus eluted by boiling the beads in Laemmli's SDS buffer and detected by western analysis using an anti-gp120 antibody (NEN Life Science Products Inc., Boston, Mass., USA). Antibody secreted into the culture medium following transient transfection of 293T was tested for virus binding in the same manner.

Figure 10:
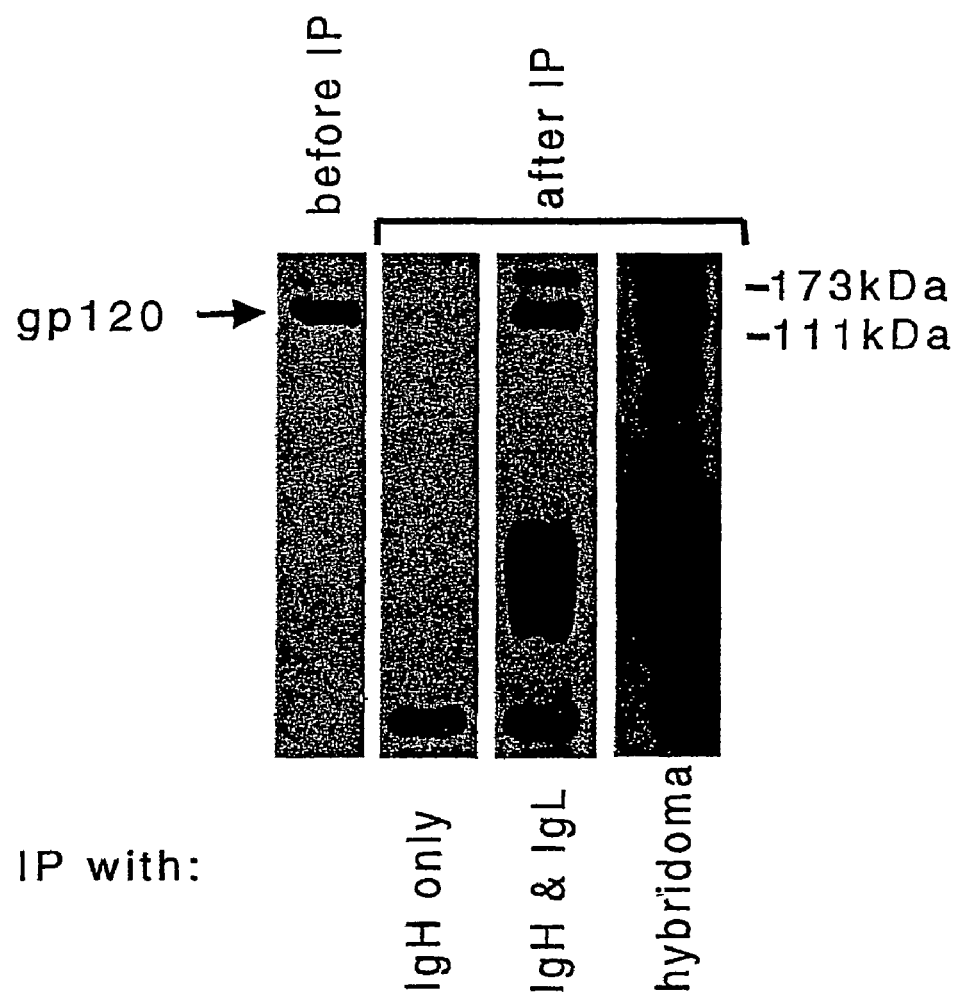
FIG. 10 illustrates the results of western analysis to detect gp120 present in HIV-1 MC99IIIBΔTat-Rev virus that had been immunoprecipitated using antibodies secreted into culture medium by hybridoma 902 or by 293T cells transiently transfected with IgL and IgH captured onto protein A/G beads. No virus was detected when culture medium from cells transfected with IgH only was used.

As shown in FIG. 10, beads which adsorbed antibodies secreted by the hybridoma or antibodies secreted by 293T cells, that were transiently transfected with IgL and IgH, were capable of binding virus. No binding of virus was observed when the cells were transfected with IgH only.

EXAMPLE 12

Cells Expressing 293-IgH-ΔCI-MPR and 293-IgH-ΔLDLR Bind and Internalize HIV-1 MC99IIIBΔTat-Rev Virus Overlay experiment were performed as described above for anti-F(ab')$_2$ antibody except that the virus was overlaid was for 1 and 3 hours followed by acid wash to remove surface-bound virus and cell fixation. Then, the cells were permeabilized for 10 minutes with 0.2% Triton-X 100, blocked for 30 min with PBS containing 1% purified BSA (Sigma), before incubation for 2 h with an anti-HIV-p24 monoclonal antibody (NEN Life Science Products Inc.), followed by incubation for 1 h with a FITC-conjugated goat anti-mouse antibody (Santa Cruz Biotechnology, Santa Cruz, Calif., USA).

Live 293-IgH-AM6PR and 293-IgH-ΔLDLR cells were overlaid with MC99IIIBΔTat-Rev virus as described above for 1 h or 3h at 37° C., followed by acid wash to remove any surface bound virus. The cells were fixed and permeabilized before staining of any virus inside the cells was performed with an anti-HIV-p24 antibody. After 1 h, strong intracellular staining was observed in both of 293-IgH-ΔCI-M6PR and 293-IgH-ΔLDLR cells but not in the parental cells. The virus appeared to be have been internalized and transported to Golgi-like intracellular structures within 1 h. After 3h, even stronger intracellular staining was observed and the cells appeared more shrunken, indicating that the internalized virus may have some cytopathic effects on the cells.

EXAMPLE 13

Cells Expressing Chimeric Antibody IgL/IgH-ΔCI-M6PR can be Infected by a Pseudotype UV Virus 293-IgH-ΔCI-MPR (clone 9) and 293-IgH-ΔLDLR (clone 10) stable clones were analyzed for surface expression of chimeric antibodies by FACScan analysis. 293-IgH-ΔCI-MPR cells showed higher surface expression of antibodies then 293-IgH-ΔLDLR (FIG. 11A). The cells were infected with a pseudotype-virus, HXB2 (He and Landau, 1995, J. Virol., 69: 4587-4592). This pseudotype virus contained a luciferase gene inserted into the nef gene and infection of cells with this reporter virus was measured by determining the amount of luciferase gene product present in lysates of the cells using commercial reagents (Promega, USA). For PMA treatment, at 84h post-infection, the infected cells were treated with 100 nM PMA for 18h before the cells were lysed and assayed for luciferase activity. 293-IgH-ΔCI-MPR showed luciferase activities (~9 fold greater than in untreated cells) only in infected cells that were treated with PMA and not in infected cells that were not treated with PMA (FIG. 11B). This indicates that 293-IgH-ΔCI-MPR cells allow the replication of internalised virus. 293-IgH-ΔLDLR cells did not show significant luciferase activities even after PMA treatment and this may be due to the lower expression of chimeric antibodies on the surface of these cells in comparison to 293-IgH-ΔCI-MPR (see FIG. 11A).

EXAMPLE 14

Materials and Methods

Sera from HCV-infected Patients

Serum samples were obtained from two patients with HCV infection being followed at the National University Hospital, Singapore. The amount of HCV RNA in these two sera were quantified by the branched DNA method (Quantiplex HCV-RNA assay; Chiron Corp. (Emeiyville, Calif., USA)) at the Molecular Diagnosis Centre, National University Hospital, Singapore, and any remaining samples were stored at $-80°$ C. The viral loads of the serum of patient A and B were $63.4 \times 10^6$ equivalents/ml and $>120 \times 10^6$ equivalents/ml, respectively. After it was confirmed that no further testing of these samples were necessary, they were transferred, with the administrating doctor's consent, to our laboratories for the experiments.

Internalization of HCV Particles $5 \times 10^5$ cells were plated on 6 cm plates and allowed to settle overnight. The cells (about 50% confluent) were washed twice with DMEM medium without FBS, followed by addition of diluted serum (100 µl of serum with 900 µl of DMEM medium without FBS), untreated or treated with detergent or pre-cleared with antibodies as described below. The cells were left for at least 8 h in a 37° C. incubator, 5% $CO_2$, before they were washed extensively with DMEM without FBS. Finally, 2 ml of complete DMEM medium was added to the cells and the cells were returned to the incubator. Two days later, the cells were trypsinized and all the cells transferred to a 15 cm plate for further incubation. Another 5 days later, the cells were trypsinized and collected and washed twice with DEPC-treated (Sigma) PBS and used immediately or stored at $-80°$ C.

For treatment with detergent, sera were diluted 10 times with DMEM medium without FBS and sterile-filtered deoxycholate solution (Sigma, 0.5% stock) was added to a final concentration of 0.05% and mixed at 4° C. for 4 h. Bio-beads (BIORAD) were prepared as described in manufacturer's protocol (using DEPC-treated PBS) and 2 ml bead slurry was added to the detergent-treated serum and incubated overnight at 4° C. This step removed the detergent from the serum to prevent any toxic effects on the cells. Then the beads were allowed to settle by gravity and the supernatant carefully remove and overlaid on the cells.

For the pre-clearing experiments, 1 ml of diluted serum (100 µl of serum with 900 µl of DMEM without FBS) was incubated with 10 µg of either anti-HCV E2 antibody (Austral Biologicals) or anti-c-myc antibody (Santa Cruz) and 100 µl of protein A/G beads (Oncogene Research Products) overnight at 4° C. After that, the beads were spun down and the supernatant overlaid on the cells. The beads were washed twice with DEPC-treated PBS and total RNA was extracted from the immuno-complexes with Trizol LS (Gibco BRL), according to the manufacturer's protocol, and resuspended in 30 µl of DEPC-treated water. Each RNA sample (neat, 10×, 30× and 100× dilutions) was tested for positive strand HCV RNA as described below.

RNA Extraction, Reverse Transcription and Nested PCR

Total RNA from $\sim 3 \times 10^6$ cells were extracted with Trizol (Gibco BRL) according to the manufacturer's protocol, and resuspended in 60 µl of DEPC-treated water. 5 µl of RNA was treated with 5 U of RNase-free DNaseI (Roche Diagnostics, GmbH, Mannheim, Germany) at 37° C. for 1 h, followed by inactivation of DNaseI by heating at 100° C. for 10 min. For the detection of positive strand HCV RNA, 5 µl of DNaseI-treated RNA was then reverse transcribed at 42° C. for 1 h using the antisense primer 209 (Table 3), dNTP (Roche) and 100 U of Superscript II RNase H reverse transcriptase (Gibco BRL) in a final volume of 10 µl, followed by inactivation by heating at 70° C. for 15 min. This product was used as template for nested PCR. The first PCR reaction was carried out using the external primers (antisense primer 209 and sense primer 939, Table 3) with 5 µl template in a total volume of 25 µl and the second round of PCR then performed using internal primer set (antisense primer 211 and sense primer 940, Table 3) with 1 µl of the first PCR reaction as template.

For the detection of negative strand HCV RNA, the tagged primer method devised by Lanford et al., Virology 202, 606-614, 1994, was used. 5 µl of DNaseI-treated RNA was reverse transcribed as above except that the tagged primer, TAGNC1 (sense, Table 3) was used instead. After inactivation of the reverse transcriptase, the template was further treated with 0.1 mg/ml of RNaseA (Sigma) at 37° C. for 30 min to degrade any remaining RNA. Then, 5 µl of the template was used for the first round of PCR using external primer set, TAG and antisense 209 (Table 3). This was followed by a second round of PCR using internal primer set, TAG and antisense 211 (Table 3), using 1 µl of the products from the first PCR as template.

Cellular GAPDH mRNA was used to check that similar number of cells was used in each experiment. For this purpose, 1 µl of DNaseI-treated RNA was then reverse transcribed as above except that oligodT (Roche) was used instead. Then 1 µl of the template was used for one round of PCR using the primers, GAPDHfor and GAPDHrev (Table 3).

All PCR were performed using Titanium Taq DNA polymerase from Clonetech Laboratories Inc. (Palo Alto, Calif., USA) in a final volume of 25 µl and PCR conditions are as follows: 95° C. for 2 min, followed by 35 cycles of 95° C. for 30 sec, 55° C. for 30 sec, 72° C. for 1 min, and a final extension at 72° C. for 10 min. Amplified products (25 µl) from the second round of PCR for positive and negative strand viral transcripts, or from one round of PCR for GAPDH, were separated on a 3% agarose gel and visualized under UV light after staining with ethidium bromide.

Southern Hybridization

For Southern blotting, the negative strand RT-PCR products were separated on agarose gel and blotted onto Hybond-N membrane (Amersham-Pharmacia Biotech). Hybridization was carried out with an oligonucleotide, corresponding to sequence in the 5'NCR(HCV probe, Table 1), 5'-labeled with [$\gamma$-$^{32}$P]dATP (NEN Life Science Products, Boston, Mass., USA) by T4 polynucleotide linase (New England Biolabs). ExpressHyb hybridization solution (Clonetech) and 10 µg/ml of sheared salmon sperm DNA (Sigma) were used for the hybridization. The filters were incubated at 60° C. for 14-16 h after which they were washed twice with 2×SSC-0.1% SDS and twice with 1×SSC-0.1% SDS, at room temperature and finally twice in 0.1×SSC-0.1% SDS, at 60° C. The filters were wrapped in SaranWrap and exposed to autoradiography films at $-80°$ C. for 12-24 h.

TA Cloning and Sequence Analysis

After separation on agarose gel, positive strand RT-PCR products were excised and purified using the QIAquick kit (Qiagen) and ligated into pCRII-TOPO vector using the TA cloning kit from Invitrogen. At least 3 clones from each ligation were sequenced (with both M15 forward and reverse primers) and confirmed to be identical. Sequences were aligned using MegAlign software (DNAStar Inc., Madison, Wis., USA).

DNA sequencing of all constructs was carried out by the core facility at the Institute of Molecular and Cell Biology. 200 ng of the double-stranded templates and 10 ng of the primer were used for the dideoxy method with the Taq DyeDeoxy terminator cycle sequencing kit and the automated DNA sequencer 373 from PE Applied Biosystems (Foster City, Calif., USA).

Results

Chimeric Receptor, TfR-CD81, Mediate Efficient Entry of HCV Particles into Huh7 Cells We tested the ability of the stable Huh7 clones to mediate HCV entry. Serum from two HCV-infected patients (A and B) were overlaid onto untransfected Huh7 or Huh7-CD81WT or Huh7-TfR-CD81 cells for a period of ~8 h, after which these cells were washed extensively and re-incubated with fresh media for 7 days. Total RNA was subsequently extracted from the cells and nested RT-PCR performed to assay for the presence of positive strand viral transcripts as an indicator of internalization of HCV particles. As the genotypes were initially not known, the sequences of primers used for RT-PCR were chosen from regions in 5' non-coding region (5' NCR) that are well conserved between all known HCV variants. These primers (Table 3) correspond to nucleotide positions (nt) 36 to 73 (sense) and nt 331 to 279 (antisense) of representative 1b isolate HCV-BK (Takamizawa et al., J. Virol. 65, 1105-1113, 1991; GenBank accession number M58335) and are similar to the ones commonly used in the literature for genotyping of HCV isolates.

FIG. 12A shows the results obtained using serum from patient A. No positive strand HCV-specific RT-PCR product was detected for untransfected Huh7 or Huh7-CD81WT cells but a strong signal was observed for Huh7-TfR-CD81 cells, showing that a significant amount of H1CV particles was internalized into Huh7-TfR-CD81 cells (FIG. 12A, panel I). When the same experiments were performed with serum from patient B, we initially found no positive strand RT-PCR products for untransfected Huh7 or Huh7-CD81WT or Huh7-TfR-CD81 cells (FIG. 12B, panel I, lane 1-3). As it has been reported that some virus particles in patient sera are heavily coated with lipoproteins and/or anti-viral antibodies (IgG), we repeated the experiment after treating the patient serum with 0.05% of a mild detergent, deoxychloate. This method was reported to remove lipoproteins/IgG gently from virus particles, resulting in enveloped virions, which can be trapped onto grids by an anti-HCV E2 antibody and visualized with electron microscopy. Remarkably, after the detergent treatment, efficient uptake of viral particles was observed for Huh7-TfR-CD81 cells but not for untransfected Huh7 or Huh7-CD81WT cells (FIG. 12B, panel I, lane 4-6).

The presence of negative strand RNA, which is an indicator of active viral replication, was examined using the strand-specific tagged RT-PCR method devised by Lanford et al., 1994. Again, no product was obtained with untransfected Huh7 and Huh7-CD81WT cells, whereas Huh7-TfR-CD81 cells showed a weak RT-PCR product under UV light after staining with ethidium bromide (FIGS. 12A and B, panel III). Further confirmation was obtained by Southern blot analysis (FIGS. 12A and B, panel IV). The low level of negative strand RNA observed may be due to a low level of replication in Huh7 cells or could be that the time-point (7 days after infection) used was not optimal. Analysis of cells collected at later time-points would be needed to address this, for example, intermittent detection of negative strand has been reported in infected primary human hepatocytes.

RT-PCR products from patient A and B (Huh7-TfR-CD81 cells) were ligated into the pCRII-TOPO vector (Invitrogen) and the sequences of the inserts were determined. Sequence of the RT-PCR product (205 bp) from patient A is identical to the corresponding 5' NCR region of representative genotype 1b, HCV-BK, sequence (Takamizawa et al., 1991; Genbank accession number M58335) and that of patient B shows two mismatches (FIG. 12C). Therefore, both patients A and B are most likely to be infected with HCV genotype 1b.

Pre-clearing of Patient Serum with an Anti-E2 Antibody Abolished Internalization of HCV Particles into Huh7-TfR-CD81 Cells.

The remaining serum of patient A was frozen after the overlay experiment described above. Here, the serum was thawed and used to test if an anti-E2 antibody, which can detect glycoslyated E2 proteins (data not shown), can immunoprecipate HCV particles from the serum. After incubating the serum with anti-HCV E2 antibody or control antibody (anti-c-myc antibody) and protein A/G beads, the beads were washed, RNA extracted, and RT-PCR performed to detect for positive strand HCV RNA associated with the beads. As shown in FIG. 13A, some viral RNA was immunoprecipated by both the anti-HCV E2 and anti-c-myc antibody. However, when we diluted the extracted RNA by 10×, 30× and 100× before performing the RT-PCR, RT-PCR products were observed only for anti-HCV E2 antibody at 10× and 30× dilutions but not for control anti-c-myc antibody, showing that amount of HCV particles immunoprecipated with the anti-HCV E2 antibody was 10 to 30 times higher than with anti-c-myc antibody (FIG. 13A).

The sera after pre-clearing with anti-HCV E2 or anti-c-myc antibody, were then used for overlaying onto Huh7-TfR-CD81 cells. The cells were then tested for presence of positive strand HCV RNA as before. As shown in FIG. 13B, anti-E2 antibody remove significant amount of viral particles from the serum such that no positive strand RT-PCR was observed in Huh7-TfR-CD81 cells that were overlaid with the serum pre-cleared with anti-E2 antibody (FIG. 13B, lane 5). In contrast, positive strand RT-PCR product was clearly detected when the serum was pre-cleared with anti-c-myc antibody (FIG. 13B, lane 6).

Here, we also repeated the overlaying experiments to compare the internalization efficiency between untransfected Huh7, Huh7-CD81WT, Huh7-TfR-CD81 and Huh7-CD81-LDLR cells. Huh7-CD81-LDLR cells were not used in the first two overlay experiments described in FIGS. 12A and B. The results showed that positive strand RT-PCR products were observed in Huh7-TfR-CD81 and Huh7-CD81-LDLR cells, but not in untransfected Huh7 or Huh7-CD81WT cells (FIG. 13B, lanes 1-4).

In summary, in 3 independent experiments (using two different patient sera), internalization of positive strand HCV RNA was consistently observed in Huh7-TfR-CD81 cells but not in untransfected Huh7 or Huh7-CD81WT cells. And in one experiment, internalization of positive strand HCV RNA into Huh7-CD81-LDLR cells was also observed. Pre-clearing of patient serum with an anti-HCV E2 antibody efficiently removed HCV particles so that no internalization of viral RNA was observed for Huh7-TfR-CD81 cells (FIG. 13B), suggesting that HCV E2 protein is the direct ligand for CD81, in agreement with previous studies. We concluded that by engineering endocytotic signal tags from transferrin and LDL receptors into either the N- or C-terminus cytoplasmic domains of CD81, we were able to trigger the uptake of viral particles in the serum of HCV-infected patients into Huh7 cells.

TABLE 3

Primers used for the detection of viral transcripts.

| Name | Sequence (5' to 3') |
|---|---|
| (SEQ ID NOS 26-34, respectively, in order of appearance) | |
| 209[2] | ATA*CTCGAG*GTGCACGGTCTACGAGACCT (nt 331-312)[1] |
| 939[3] | CTGTGAGGAACTACTGTCTT (nt 36-55)[1] |
| 211[2] | CAC*TCTCGAG*CACCCTATCAGGCAGT (nt 294-279)[1] |
| 940[3] | TTCACGCAGAAAGCGTCTAG (nt 54-73)[1] |
| TAGNC1 | TCATGGTGGCGAATAAACTCCACCATAGATCACTCC (nt 15-34)[1] |

TABLE 3-continued

Primers used for the detection of viral transcripts.

| Name | Sequence (5' to 3') |
|---|---|
| TAG | TCATGGTGGCGAATAA |
| HCVprobe | GCAGAAAGCGTCTAGCCATGGCGTTAGTAT (nt 59-88)[1] |
| GAPDHfor | CTGAGAACGGGAAGCTTGTCATCA |
| GAPDHrev | CGTCTAGCTCAGGGATGACCTTG |

[1]All HCV nucleotide positions (nt) are with reference to a representative genotype 1b isolate, HCV-BK (17, Genbank accession number M58335). Sequences corresponding to restriction sites are indicated in italics.
[2]Sequence is the same as primers used in Garson et al, Lancet 336, 878-879, 1990.
[3]Sequence is the same as primers used in Okamoto et al., Jpn. J. Exp. Med. 60, 215-222, 1990.

The invention claimed is:

1. A chimeric transmembrane protein comprising:
   (i) an extracellular domain capable of binding a virus;
   (ii) an intracellular internalisation signal, and
   (iii) a transmembrane domain,
wherein the chimeric transmembrane protein when expressed by a cell is capable of internalizing into said cell a virus bound to the extracellular domain.

2. A protein according to claim 1, wherein said extracellular domain is an antibody fragment.

3. A protein according to claim 2, wherein said antibody fragment comprises a variable region of an antibody heavy chain and a variable region of an antibody heavy chain.

4. A protein according to claim 1 wherein said extracellular domain comprises a cell-surface receptor, or fragment thereof, capable of binding to a viral coat protein.

5. A protein according to claim 1 wherein said virus is selected from the group consisting of HCV, HIV, HBV, RSV, influenza virus, herpes simplex virus, rabies virus, coxsackie virus and rhinovirus.

6. A protein according to claim 1 wherein said virus is HIV.

7. A protein according to claim 6 wherein said extracellular domain is an antibody to gp120/160, or a fragment of said antibody.

8. A protein according to claim 6 wherein said extracellular domain is CD4, or a fragment thereof capable of binding HIV.

9. A protein according to claim 1, wherein said virus is HCV.

10. A protein according to claim 9 wherein said extracellular domain is an antibody to E2 protein or a fragment of said antibody.

11. A protein according to claim 9 wherein said extracellular domain is CD81, or a fragment thereof capable of binding HCV.

12. A protein according to claim 1 wherein said internalisation signal is from a constitutively recycling receptor.

13. A protein according to claim 12 wherein said receptor is selected from the group consisting of low density lipoprotein receptor (LDLR), transferrin receptor (TFR), cation-dependent mannose-6-phosphate receptor (CD-Man-6-PR), cation-independent mannose-6-phosphate receptor (CI Man-6-PR), poly Ig receptor and asialo gylcoprotein receptor (ASGPR) H1 subunit.

14. A protein according to claim 12 wherein said protein comprises the entire intracellular domain of said receptor.

15. A protein according to claim 12 wherein said protein comprises a fragment of said receptor.

16. A protein according to claim 15, wherein said fragment is from 4 to 40 amino acids long.

17. A protein according to claim 12 wherein said protein comprises a chimeric intracellular domain comprising a fragment of each of two or more constitutively recycling receptors.

18. An isolated polynucleotide encoding a protein according to claim 1.

19. A vector comprising a polynucleotide according to claim 18.

20. An isolated cell comprising a protein according to claim 1.

21. A method of producing a cell comprising the protein of claim 1, said method comprising transfecting a cell with a polynucleotide encoding the protein or a vector comprising a polynucleotide encoding the protein and maintaining said cell under conditions suitable for obtaining expression of the protein.

22. An isolated cell according to claim 20 which is infected with a virus capable of binding to the extracellular domain of said protein.

23. An isolated cell according to claim 22 which is a non-human cell.

24. An isolated cell according to claim 22 which cell is a liver cell and wherein said virus is HCV.

25. An isolated cell according to claim 22, wherein said virus is HIV.

26. A method of producing a cell according to claim 22, which method comprises contacting a cell according to claim 20 with a virus under conditions suitable for binding of said virus to said protein.

27. A method for identifying an anti-viral agent, said method comprising:

(i) providing an isolated cell according to claim 22

(ii) contacting said cell with a test agent; and (iii) monitoring viral infection thereby determining whether the test agent has anti-viral activity.

28. A method of identifying an anti-viral composition capable of inhibiting viral infection, which method comprises:
   (i) providing an isolated cell according to claim 20;
   (ii) contacting said cell with a test agent;
   (iii) contacting said cell with a virus capable of binding to said protein; and
   (iv) determining whether the test agent limits viral infection.

29. A method according to claim 27 wherein (iii) comprises one or more of the following:
   (a) monitoring cell death;
   (b) monitoring viral replication;
   (c) monitoring protein synthesis; and
   (d) monitoring presence of viral protein on the surface of said cells.

30. A method according to claim 29 wherein said viral infection is a HCV or HIV infection.

31. A method according to claim 28 wherein (iii) or (iv) comprises one or more of the following:
   (a) monitoring cell death;
   (b) monitoring viral replication;
   (c) monitoring protein synthesis; and
   (d) monitoring presence of viral protein on the surface of said cells.

32. The method according to claim 27 wherein said viral infection is a HCV or HIV infection.

33. The method according to claim 28 wherein said viral infection is a HCV or HIV infection.

34. A protein according to claim 1 wherein said protein is a single polypeptide.

* * * * *